(12) United States Patent
Toth

(10) Patent No.: US 10,709,825 B2
(45) Date of Patent: Jul. 14, 2020

(54) WOUND EXUDATE MONITOR ACCESSORY

(71) Applicant: ConvaTec Technologies Inc., Las Vegas, NV (US)

(72) Inventor: Landy Aaron Toth, Newton, PA (US)

(73) Assignee: ConvaTec Technologies Inc., Las Vegas, NV (US)

( * ) Notice: Subject to any disclaimer, the term of this patent is extended or adjusted under 35 U.S.C. 154(b) by 0 days.

(21) Appl. No.: 15/353,608

(22) Filed: Nov. 16, 2016

(65) Prior Publication Data

US 2017/0065751 A1 Mar. 9, 2017

Related U.S. Application Data

(63) Continuation of application No. 13/992,642, filed as application No. PCT/US2011/063784 on Dec. 7, 2011, now Pat. No. 9,526,816.

(Continued)

(51) Int. Cl.
*A61M 1/00* (2006.01)
*A61B 5/145* (2006.01)
(Continued)

(52) U.S. Cl.
CPC ....... *A61M 1/0031* (2013.01); *A61B 5/14539* (2013.01); *A61B 5/14557* (2013.01);
(Continued)

(58) Field of Classification Search
None
See application file for complete search history.

(56) References Cited

U.S. PATENT DOCUMENTS 9,440,963 B2 9/2016 Peters et al.
9,526,816 B2 12/2016 Toth et al.
(Continued)

FOREIGN PATENT DOCUMENTS

JP 2004265269 A 9/2004
JP 2005293241 A 10/2005
(Continued)

OTHER PUBLICATIONS

Chinese Patent Application No. 201180067112.3 First Office Action dated Mar. 12, 2015.
(Continued)

*Primary Examiner* — Matthew D Krcha
(74) *Attorney, Agent, or Firm* — Taft Stettinius & Hollister LLP; Ryan O. White

(57) ABSTRACT

A stand-alone system for assessing wound exudates from the wound of a patient is described. The system contains functionality to detect, process and report various wound parameters. The system also may make treatment determinations based on these findings. The system may detect one or more physiological values of the wound exudates from the wound of the patient. The system may also compare detected physiological values to predetermined physiological values, in order to obtain a comparison result in real time. The system may include a processor (15) which provides an electronic signal based on the comparison result in which the electronic signal may corresponds to guidelines for treating the wound (3). The system described may be an accessory, which may be used on its own, or in conjunction with other wound treatment devices (9).

20 Claims, 12 Drawing Sheets

Related U.S. Application Data

(60) Provisional application No. 61/420,996, filed on Dec. 8, 2010.

(51) Int. Cl.
    *A61B 5/1455* (2006.01)
    *A61B 5/00* (2006.01)
    *A61B 5/01* (2006.01)

(52) U.S. Cl.
    CPC .......... *A61B 5/445* (2013.01); *A61M 1/0088* (2013.01); *A61B 5/0075* (2013.01); *A61B 5/01* (2013.01); *A61M 2205/18* (2013.01); *A61M 2205/332* (2013.01); *A61M 2205/3306* (2013.01); *A61M 2205/3334* (2013.01); *A61M 2205/3344* (2013.01); *A61M 2205/3379* (2013.01); *A61M 2205/3389* (2013.01); *A61M 2205/3592* (2013.01); *A61M 2205/52* (2013.01); *A61M 2230/005* (2013.01); *A61M 2230/208* (2013.01); *A61M 2230/50* (2013.01)

(56) References Cited

U.S. PATENT DOCUMENTS

| | | |
|---|---|---|
| 2001/0029956 A1 | 10/2001 | Argenta et al. |
| 2002/0143286 A1 | 10/2002 | Tumey |
| 2002/0161317 A1 | 10/2002 | Risk et al. |
| 2004/0073151 A1 | 4/2004 | Weston |
| 2005/0192548 A1 | 9/2005 | Dolliver et al. |
| 2006/0173253 A1 | 8/2006 | Ganapathy et al. |
| 2006/0234319 A1 | 10/2006 | Kakui et al. |
| 2007/0118096 A1* | 5/2007 | Smith .................. A61B 5/445 604/541 |
| 2008/0146906 A1 | 6/2008 | Baker et al. |
| 2008/0269582 A1 | 10/2008 | Mansour et al. |
| 2008/0278336 A1 | 11/2008 | Ortega et al. |
| 2009/0177051 A1 | 7/2009 | Arons et al. |
| 2010/0022990 A1 | 1/2010 | Karpowicz et al. |
| 2010/0030132 A1 | 2/2010 | Niezgoda et al. |
| 2012/0129269 A1 | 5/2012 | Choi, II et al. |

FOREIGN PATENT DOCUMENTS

| | | |
|---|---|---|
| JP | 2009525776 A | 7/2009 |
| JP | 2010-510837 A | 4/2010 |
| JP | 2010531700 A | 9/2010 |
| WO | WO-2004040273 A1 | 5/2004 |
| WO | WO-2007062024 A1 | 5/2007 |
| WO | WO-2007092397 A2 | 8/2007 |
| WO | WO-2008048481 A2 | 4/2008 |
| WO | WO-2008064502 A1 | 6/2008 |
| WO | WO-2008100671 A1 | 8/2008 |
| WO | WO-2009039203 A2 | 3/2009 |
| WO | WO-2009141820 A1 | 11/2009 |
| WO | WO-2010011920 A2 | 1/2010 |
| WO | WO-2012078781 A1 | 6/2012 |
| WO | WO-2012078784 A1 | 6/2012 |

OTHER PUBLICATIONS

Chinese Patent Application No. 201180067112.3 Search Report dated Jan. 20, 2014.
European Patent Application No. 11847037.6 Communication dated Jul. 21, 2016.
European Patent Application No. 11847037.6 Communication dated Jul. 23, 2015.
European Patent Application No. 11847037.6 extended European Search Report dated Aug. 21, 2014.
Japanese Patent Application No. 2013-543319 Office Action dated Sep. 27, 2016.
Japanese Patent Application No. 2013-543319 Office Action dated Jun. 29, 2015.
Japanese Patent Application No. 2013-543319 Office Action dated Nov. 4, 2014.
PCT /US2011/063784 International Preliminary Report on Patentability dated Jun. 12, 2013.
PCT/US2011/063784 International Search Report completed Mar. 9, 2012.
PCT/US2011/063784 Written Opinion completed Mar. 9, 2012.
U.S. Appl. No. 13/992,642 Office Action dated Dec. 18, 2015.
U.S. Appl. No. 13/992,642 Office Action dated Jul. 15, 2015.
U.S. Appl. No. 13/992,642 Office Action dated Mar. 25, 2015.
Canadian Patent Application No. 2,819,475 Examination Report dated Oct. 4, 2017.
Canadian Patent Application No. 2,819,549 Office Action dated Oct. 4, 2017.
Japanese Patent Application No. 2017-013321 Office Action dated Jan. 9, 2018.
U.S. Appl. No. 13/992,637 Office Action dated Jun. 14, 2017.
U.S. Appl. No. 13/992,637 Office Action dated Sep. 25, 2017.
Chinese Patent Application No. 201180067100.0 First Office Action dated Jan. 28, 2015.
Chinese Patent Application No. 201180067100.0 Search Report dated Jan. 20, 2015.
European Patent Application No. 11847022.8 Communication dated Sep. 2, 2016.
Japanese Patent Application No. 2013-543318 Decision of Rejection dated Dec. 10, 2015.
Japanese Patent Application No. 2013-543318 Office Action dated Nov. 4, 2014 (English language translation provided on Jul. 5, 2015 and attached herewith).
PCT Patent Application No. PCT/US2011/063781 International Preliminary Report on Patentability dated Jun. 12, 2013.
PCT Patent Application No. PCT/US2011/063781 International Search Report dated Mar. 21, 2012.
PCT Patent Application No. PCT/US2011/063781 Written Opinion dated Mar. 21, 2012.
U.S. Appl. No. 13/992,637 Office Action dated Jan. 15, 2016.
U.S. Appl. No. 13/992,637 Office Action dated May 6, 2015.
U.S. Appl. No. 13/992,637 Office Action dated Oct. 7, 2016.
European Patent Application No. 11847022.8 Communication dated Feb. 10, 2017.
European Patent Application No. 11847037.6 Communication dated Mar. 22, 2017.
Japanese Patent Application No. 2016-086432 Office Action dated Mar. 14, 2017.

* cited by examiner

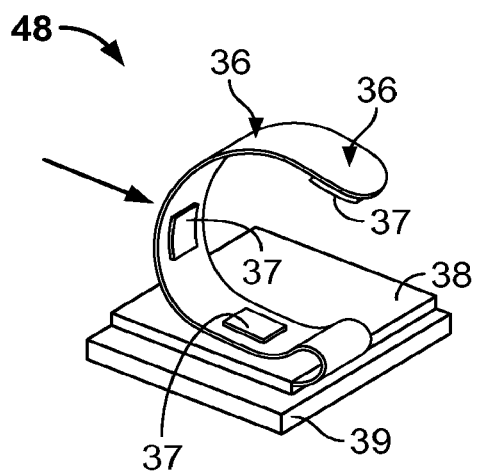
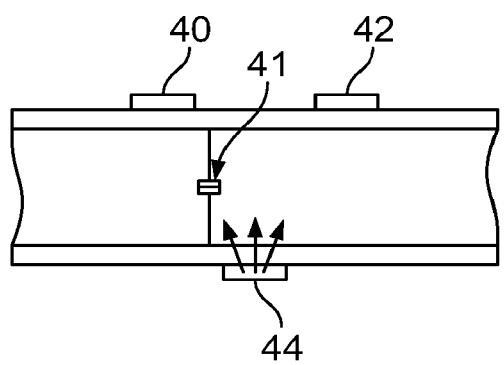
FIG. 5      FIG. 6
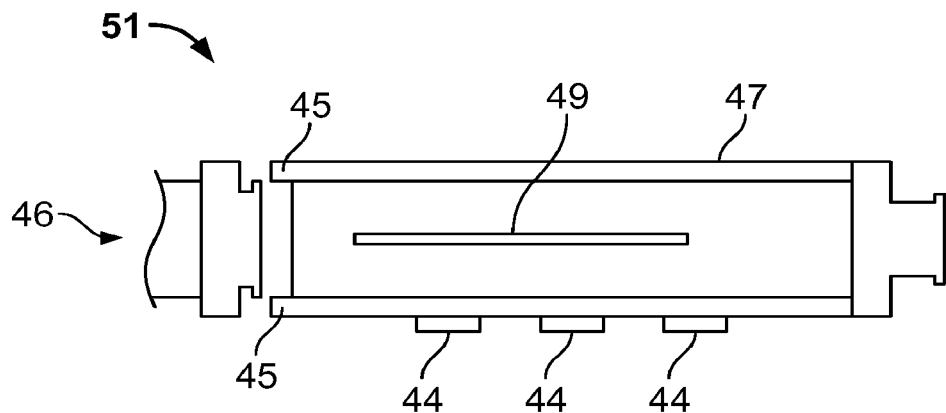
FIG. 7
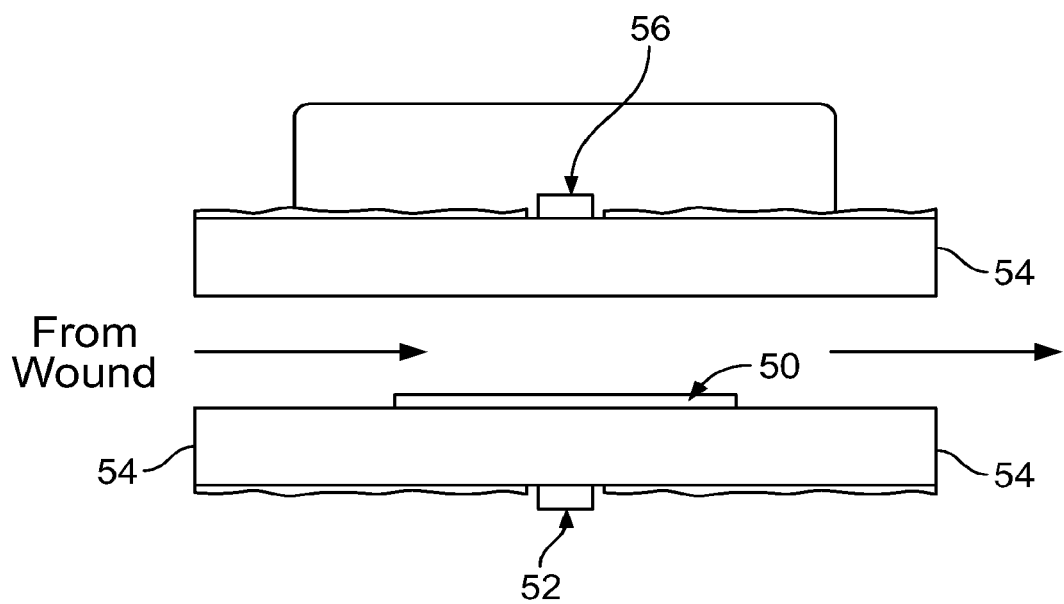
FIG. 8

WOUND EXUDATE MONITOR ACCESSORY

CROSS-REFERENCE TO RELATED APPLICATIONS

This application is a continuation application of U.S. patent application Ser. No. 13/992,642, filed on Jul. 26, 2013, now U.S. Pat. No. 9,526,816 issued Dec. 27, 2016, which is a U.S. National Phase of PCT/US2011/063784, filed Dec. 7, 2011, which claims the benefit of U.S. Provisional Application No. 61/420,996, filed on Dec. 8, 2010, each of which is entirely incorporated herein by reference.

BACKGROUND OF THE INVENTION

There is a need to autonomously monitor and assess the negative pressure wound therapy ("NPWT") process and to provide a mechanism to interrupt the NPWT therapy in cases where a contraindication develops in the patient during use. There is also a further need to improve upon certain features of NPWT devices, such as safety, functionality and intelligent, real time feedback.

Current treatment protocols for assessing wound state involve the qualitative analysis by caregivers. Often, a caregiver will assess the condition of a wound by the way it looks or smells or the overall appearance of the exudates. Many times, however, the caregiver is not assessing the wound regularly or quantitatively. Such assessment may only occur at daily or weekly intervals, for example. A disadvantage to this treatment protocol is that the assessment is of old exudates. The physiological parameters of these exudates may change over time when compared to their original state in the wound. Color, microbes, oxygen, and temperature all change over time, so the assessment of the exudates at a time after they have been collected is not an accurate or reliable prediction of wound condition. Additionally, the flow of exudates may be a useful tool in wound assessment. Prior assessment techniques do not offer a viable solution for monitoring wound exudates flow.

There is a further need to provide a wound assessment system that may be added on to existing wound treatment devices, such as negative wound pressure therapy devices.

SUMMARY OF THE INVENTION

In accordance with an aspect of the invention, a standalone system for assessing wound exudate from the wound of a patient may comprise detecting means for detecting one or more physiological values of the wound exudates from the wound of the patient. The system may also comprise comparing means for comparing the one or more detected physiological values to one or more predetermined physiological values to obtain a comparison result in real time and a processor to provide an electronic signal based on the comparison result. The electronic signal may correspond to guidelines for treating the wound.

In accordance with another aspect of the present invention, a stand-alone system for assessing wound exudates from a wound of a patient is disclosed. The system may comprise various features, including a wound treatment device and sensors or detectors. The sensors or detectors detect or sense one or more values of one or more physiological parameters of the wound exudate. The system may also comprise a processor to analyze the values of the one or more physiological parameters, so as to obtain an assessment of the wound exudate and provide a treatment guideline based on the assessment. In accordance with this particular embodiment, the sensors or detectors, and the processor attach to the wound treatment device.

DESCRIPTION OF THE DRAWINGS

FIG. 5 depicts a wound exudate system containing sensors on a flexible circuit substrate, in accordance with an embodiment of the present invention.

FIG. 6 depicts a wound exudate system that contains a flow disruption element, in accordance with an embodiment of the present invention.

FIG. 7 depicts a removable wound exudate system that may be spliced into a wound treatment line, in accordance with an embodiment of the present invention.

FIG. 8 depicts a wound exudate system containing an inflow feature with a biomarker coating, in accordance with an embodiment of the present invention.

DETAILED DESCRIPTION

A system, apparatus and method for monitoring and assessing wound exudates are disclosed herein. The system and apparatus ("wound exudate system" or "system") allow for convenient assessment of wound exudates from a wound site and may provide real time quantitative and predictive functionality. The system may be a stand-alone unit or be used in conjunction with other wound treatment devices, by various methods of attachment.

A wound treatment device may be any active device. The system may be packaged as an entirely separate device from any wound treatment device, including, a negative pressure wound therapy (NPWT) device, or any passive device, such as a bandage or dressing.

In addition, a system and method for collecting physiological data, and predicting wound healing outcomes based on trends of values of exudate flow rate and other characteristics are also disclosed.

Figure 1:
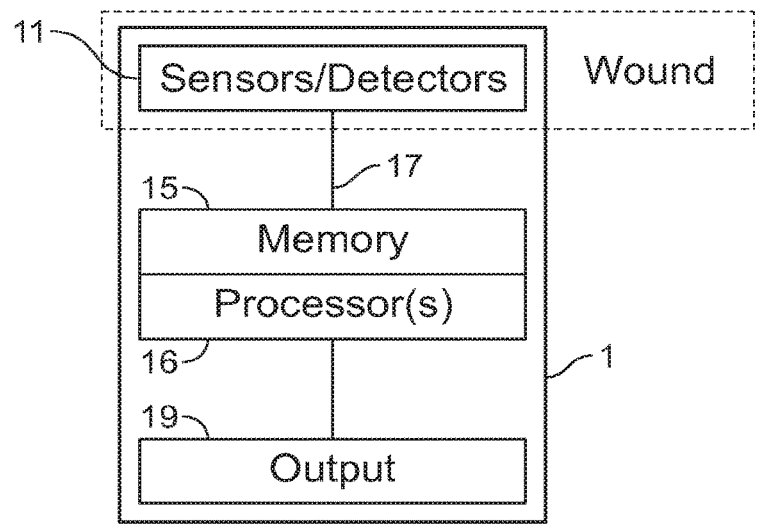
FIG. 1 is a functional block diagram representing components of a wound exudate system, in accordance with an embodiment of the present invention.

FIG. 1 is a block diagram of an embodiment of a wound exudate system 1, in accordance with the present invention. In this embodiment, sensors or detectors 11 may detect and retrieve data representing the condition of a wound. This wound data may be transferred electronically via wired or wireless communication means 17 to one or more processors 15. The processors may, among other things, predict wound state and other treatment solutions, based on the wound data. Optionally, data may be stored in a memory 16. Information from the processor(s) 15 may be transmitted to an output device 19 by any means known in the art, in order to inform or alert a user about the health or state of a wound.

Figure 1A:
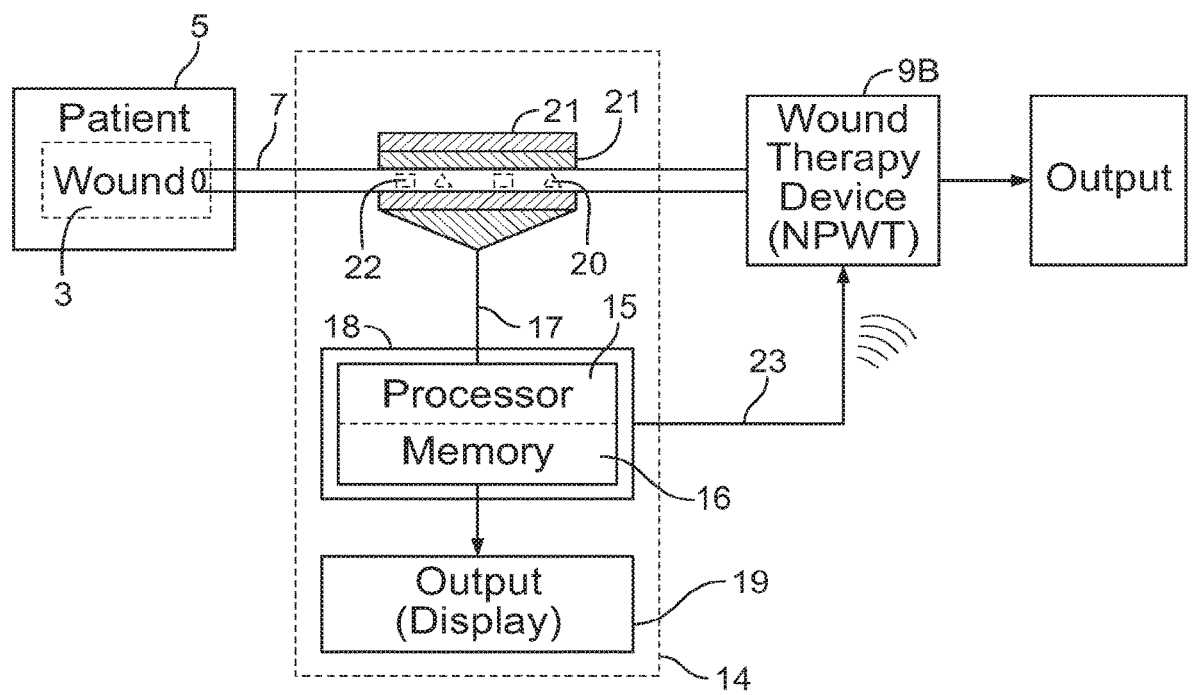
FIG. 1a shows an embodiment of a wound exudate system as an accessory to an NPWT device, in accordance with an embodiment of the present invention.

FIG. 1a depicts an embodiment of a wound exudate system 14 which is a stand-alone accessory designed to be attached to any existing wound therapy device. In accordance with an aspect of the present invention, the system 14 may be in fluid communication with a wound 3 (and wound exudate) of a patient 5. Fluid communication between the system 14, and the wound 3 may be by any means known in the art (e.g., a wound drain 7, that is part of a wound therapy device 9). In this embodiment, the system 14 generally comprises an attachment element 21 for attaching to an existing drain line 7 of a wound therapy device. Attachment element 21 may take on multiple configurations as described subsequently herein and is by no means limited to one particular structural adaptation. The attachment element 21 may be any type of clip, tube, clamp, patch, insert, cradle, tube, adhesive or any other attachment means conceivable.

The system 14 may optionally contain one or more light sources 22 and detectors and or sensors 20 for emitting and detecting light at various wavelengths. The sensors 20 and sources 22 may be capable of transmitting and receiving signals through existing wound drains. As described subsequently herein, the sensors 20 may be of any type commonly known in the art, including but not limited to pressure, temperature, and pH sensors. The information obtained by the sensors 20 may be transmitted by wired or wireless means 17 known in the art and as described subsequently herein. The data from the sensors are subsequently received and processed by processor(s) 15.

Also contained within the accessory wound exudate system 14 is a memory 16. This memory may be of any type commonly known in the art and may be employed to store any type of useful data such as historical data, instructions of process performed by the processor(s) 15, and spectral maps. The memory 16 may also be used to store values of the data signals by the sensors 20. The processor(s) 15 and memory 16 may be contained within any type of housing 18. Housing 18 may also contain any necessary power supply and electronic circuitry needed for operation of the system 14.

Based on processing the data received from sensors 20, the processor(s) 15 of the wound exudate system 14, may derive either a current state of the wound and/or one or more treatment options for the wound. In one embodiment, based on a determination from the processing, real time treatment options and diagnoses may be performed. The system 14 may also provide a command or signal 23 to a wound therapy device such as an NPWT device 9B.

Information from the system 14 is optionally outputted on an output device 19. Such an output device may be integral within the system 14 or a display located remote from the system. The output device 19 from the wound exudate system 14 may be on any device known to those of ordinary skill in the art. For example, certain threshold measurements may necessitate a device capable to provide an audible or visual alert in the form of a buzzer or light indicator, or a visual display such as an LCD.

Such system 14 is advantageous in that it provides a functional add-on approach for monitoring a wound already being treated by a wound therapy device. In instances when a wound therapy device, such as an NPWT, is already in use and the wound therapy device does not provide wound monitoring, the system 14 may provide a useful monitoring and treatment solution.

Figure 1B:
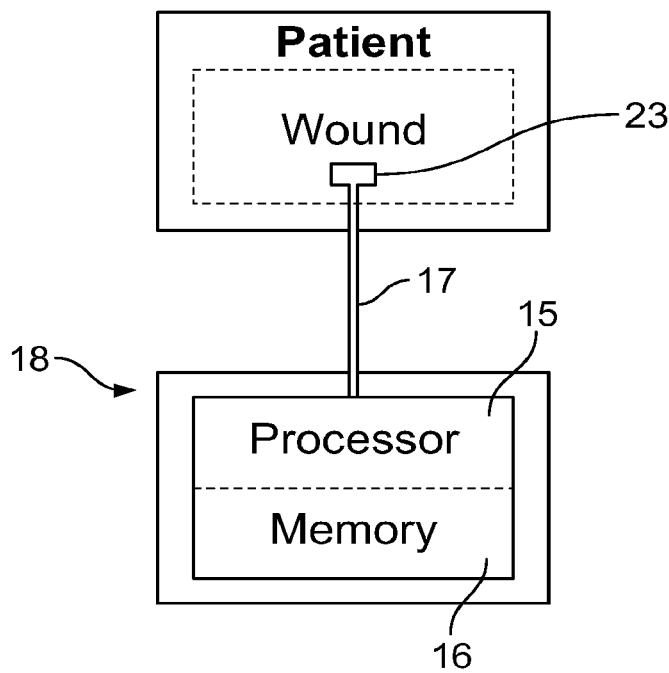
FIG. 1B shows a stand-alone wound exudate system, in accordance with an embodiment of the present invention.

FIG. 1B depicts an embodiment of an accessory wound exudate system 18, which may be used without a wound treatment device such as a bandage or NPWT. In this embodiment, one or more sensors 23 may be placed directly into or near a wound. The sensors 23 may then collect and transmit data, via communication means 17, regarding wound parameter measurement to a wound exudate system 18, where the signals and data may be processed and analyzed in accordance with aspects of the invention.

The system 18 may detect the presence of blood in the exudates as well as monitor and assess other physiological values relevant to wound exudates, such as flow rate/quantity, color, bacterial traces, temperature, pH and the like.

Figure 1C:
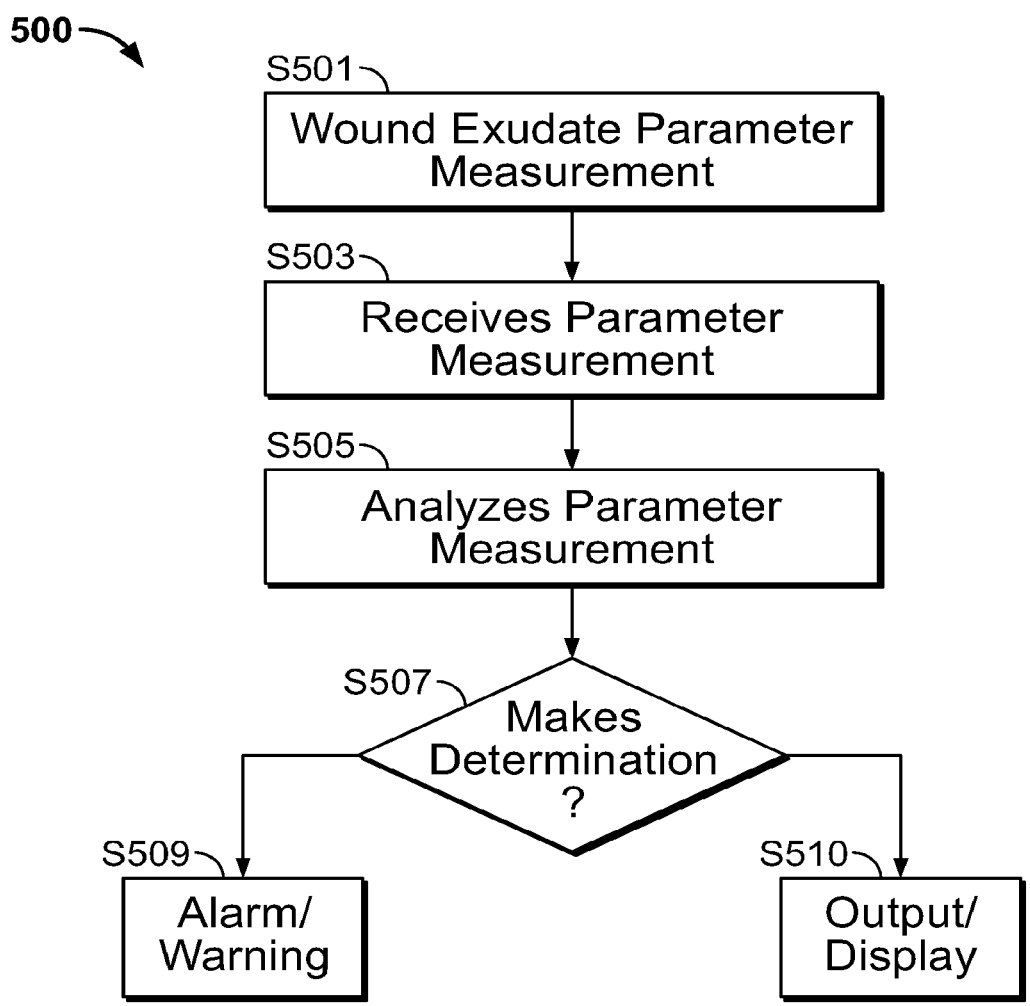
FIG. 1C is flow diagram of a wound assessment process, in accordance with an embodiment of the present invention.

FIG. 1C is a flow diagram illustrating an exemplary wound exudate system process 500. The blocks in FIG. 1C are representative of various functions of a wound exudate system, which may be combined, omitted, added, or reordered as suitable.

In block S501, sensors detect and/or measure one or more parameters of the wound exudate. Measurement data obtained in block S501 is transmitted to and received by one or more processors in block S503. The processors then analyze the received data in block S505. Based on results of analyzing, in block 507 determination(s) is made regarding the measurements by the sensors. Those determinations, which may include a diagnosis or treatment guideline, are then output via an alarm or warning in block S509, or an output display in block S510.

Figure 2:
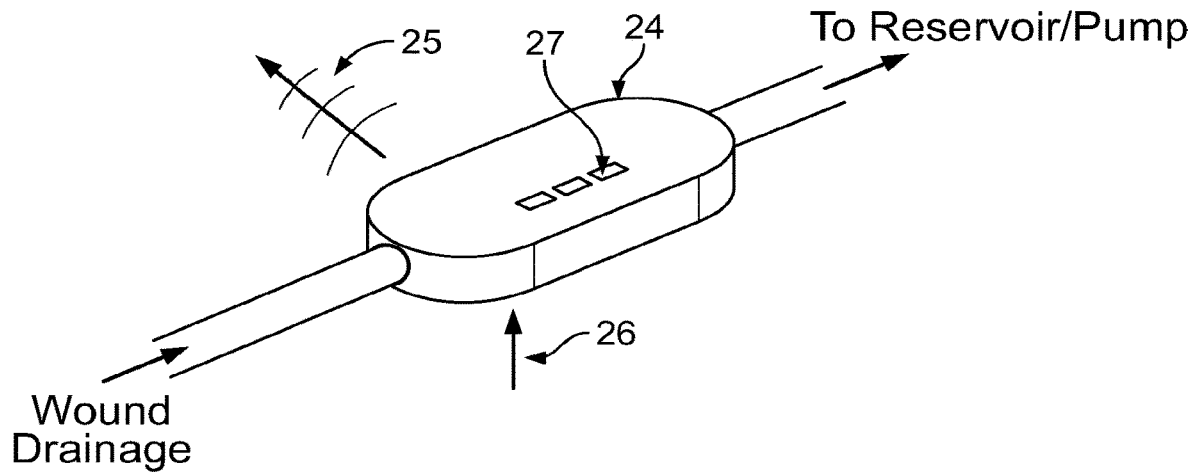
FIG. 2 shows a wound exudate system disposed, on a wound drain, in accordance with an aspect of the invention, in accordance with an embodiment of the present invention.

In one embodiment, the exudates system may be configured for attachment to an existing wound drainage line, by clamping onto the drainage line of the NPWT device, and may be fully isolated from wound exudates. Thus, the system may be reused across multiple dressing changes and even multiple patients in its entirety. In this embodiment, the exudates system 26 may be mounted on the wound drainage line, as indicated in FIG. 2. The system 26 may contain optional wireless communication capabilities 25 and indicators 27 for indicating the presence or absence of a given condition.

Figure 3:
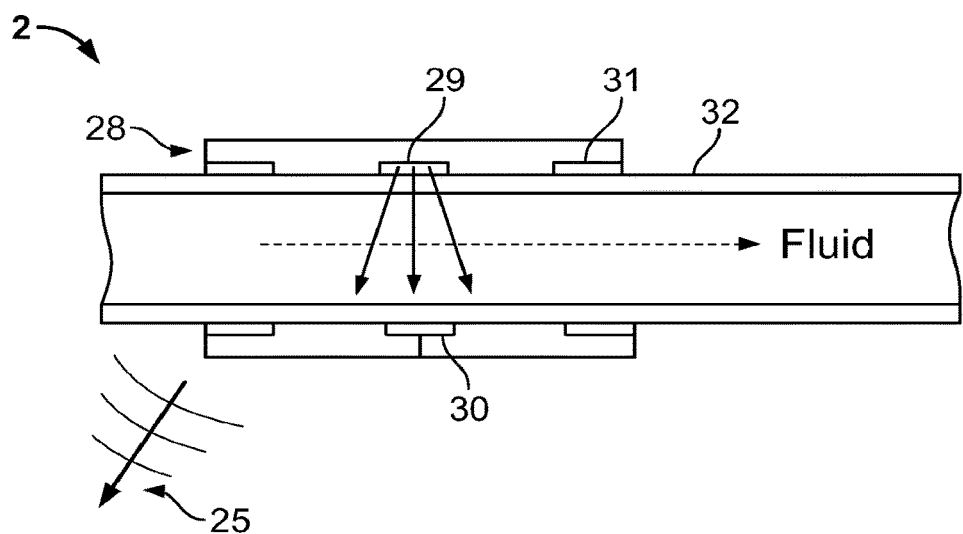
FIG. 3 depicts a cross-sectional view of a wound exudate system, in accordance with an embodiment of the present invention

FIG. 3 depicts an embodiment of a wound exudate system 28 integrated into an existing wound drain line. The system contains a light source 29 for emitting light of a certain wavelength(s) into the exudate. The system also contains a detector 30 for detecting and/or sensing the emitted wavelengths of light after it has passed through wound exudate. Amplitude of the detected wavelengths represent the spectral attributes of the exudates and may be indicative of wound state.

Additionally, the embodiment depicted by FIG. 3 depicts an optical barrier 31 disposed on the exterior of a wound drainage line 32. The optical barrier 31 is useful for avoiding ambient light from reaching the wound exudate. This increases the accuracy of the detection, as it avoids any artifacts that may be caused by light other than that emitted by the source 29. Results may be transmitted via communication means 25.

Figure 4:
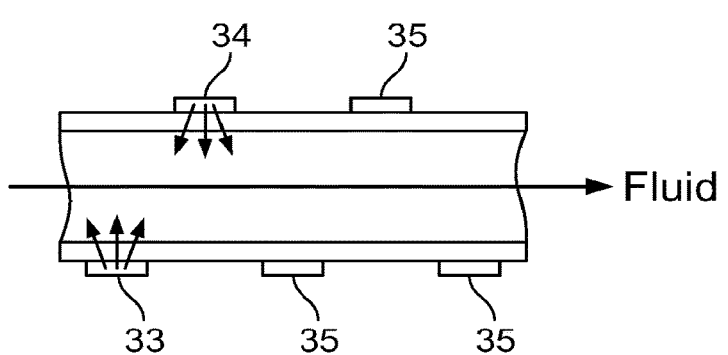
FIG. 4 depicts an embodiment of a wound exudate system containing multiple light sources and multiple detectors, in accordance with an embodiment of the present invention.

FIG. 4 depicts another alternative embodiment of the present invention, in which the system may contain multiband sources of light, including a narrowband source 33 and a broadband source 34. Multiple multiband detectors 35 may also be disposed within the system. Multiband sources and detectors may be useful for detecting various wavelengths of light and therefore different attributes of the exudates. The detectors 35 may be configured to remove unwanted ambient light and obtain more complete spectral information.

In another embodiment, the system comprises a small clip-on element that may be placed around the tube (not shown) of a wound drain, as seen in FIG. 5, or attached to a connector of a wound drain. Some representative sensor configurations are shown in the FIGS. 3, 4, 5, and 6.

In general, optical sensors and sources may be arranged around the tube of a wound drain, pointing inwards toward the lumen of the drain, so as to assess light after it has propagated through the fluid in the tube.

Referring to FIG. 5, a wound exudate system 48 is a stand-alone system including a small patch that may be attached to the outer surface of a wound dressing or cover dressing. In one embodiment, sensors and sources 37 may be arranged on an interior of a flex circuit substrate 36, or any type of flexible substrate or platform capable of attaching to a wound drain. The system 48 also contains control circuitry 38 disposed on or near a battery 39, or alternate power source. This configuration allows for a wound drain tube to be advanced through the opening of the flexible circuit substrate and remain in close proximity with the sources and detectors 37, and held in a secure pressure fit relationship by the flexible circuit substrate.

In another embodiment, suitable for use in hospital setting, an exudates system may be attached to a central suction system. In this case, the exudates system may be associated and operated in tandem with an existing central suction system, so as to warn and shutdown flow from the wound site in the case of an adverse event. In this case, the exudates system may clamp the wound drainage line in the case of an adverse event. Such an embodiment may provide a safe and low cost alternative to existing NPWT devices in a hospital setting. This mechanism may be useful in preventing inadvertent hemorrhagic crises created by undetected bleeding. In this case, the central suction unit may be pre-configured with an integrated wound system as described herein.

In certain other embodiments, an accessory exudate assessment system may be configured to slide onto a feature of an existing wound treatment device, such as a wound drain, attach with adhesive, click into a feature, straddle a suction port, etc. The dressing may have a feature on the outside surface with which the system may interface for placement onto the outside of a dressing element.

FIG. 6 depicts an alternative embodiment of a wound exudate system that contains a flow disruption element 41 in combination with one or more detectors 40 and 42 and a source 44. The arrangement of the present embodiment may provide more accurate sensing, based on the deflection of the flow disruption element.

In one embodiment, an exudates system may comprise a fluid channel through which exudates may pass. In this case, the fluid channel may further comprise an obstruction 41 located in the path of the exudates, as seen in FIG. 6. As exudates pass the obstruction, a disturbance in the flow is created. The behavior of the flow in and around the disturbance may be useful for measuring parameters of the flow, such as viscosity, concentration and/or composition of solid matter, etc. The disturbance in the flow may also be used to better mix the exudate, which may be useful for improving measurement accuracy. Any signal variation between detectors 40 and 42 may be related to the flow disruption element. Viscosity may also be used to determine general water content of the exudates, as well as the presence of large molecules.

FIG. 7 depicts, a system 51 configured for attachment to, and detachment from an existing wound line 46. Portion 47 of the system 51 is removable and also disposable. An optional inflow disruption element 49 may also be present to further optimize detection performance. As an inline diagnostic system as seen in FIG. 7, the exudates system 51 may detect traces or values of bacteria, color changes, presence of necrotic tissue, changes in values of exudates flow rate, changes in temperature values of the exudates, and the like that could be an early indication of a change in the wound state. Furthermore, the inline diagnostic system 1H may allow for early detection of contra-indications such as bleeding, thus allowing a caregiver to promptly and appropriately adjust the treatment.

Figure 21:
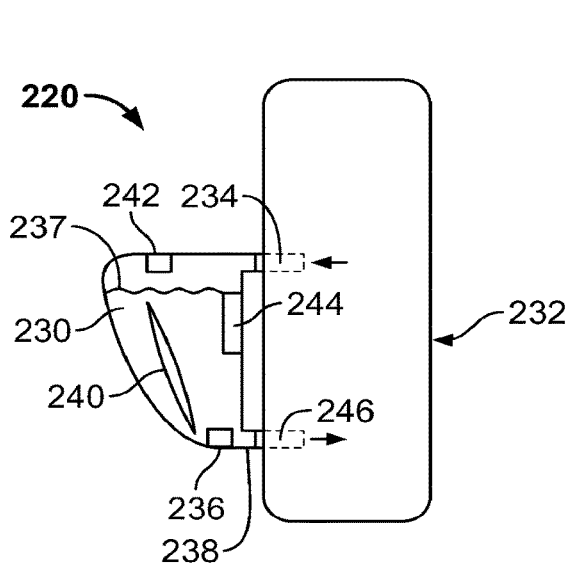
FIG. 21 illustrates an alternative embodiment of a wound exudate system disposed within an ancillary collection chamber, in accordance with an embodiment of the present invention.

In another embodiment of the present invention, an exudate assessment system may be attached to an exudate collection canister. It may also have structures and shaped tubes in the flow path to ensure that the fluid under analysis does not mix with previously collected exudates prior to being assessed, as seen in FIGS. 16 and 21.

Figure 16:
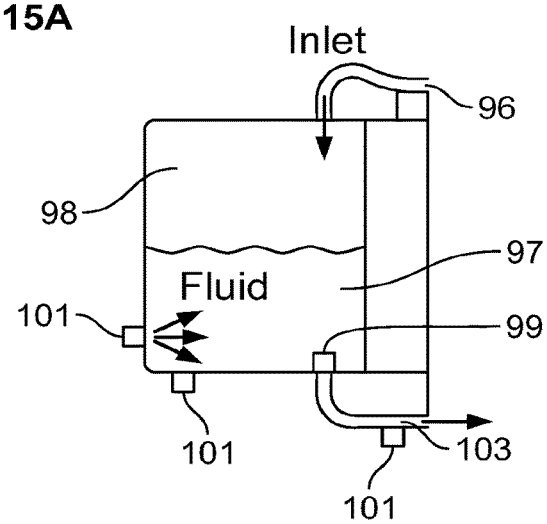
FIG. 16 depicts a wound exudate system configured within a collection chamber, in accordance with an embodiment of the present invention.

In yet another embodiment, the exudates system may have a chamber or trap 98, as seen in FIG. 16, into which fluids 97 may pool, or flow so as to assist with obtaining more precise measurements regarding the physical state of the exudates. Measurements, such as flow rate may be taken of the pooled fluid, the flowing fluid, or both by sensors 101. This embodiment may be particularly useful for measuring the thermal mass of the exudate.

The exudates system may also comprise a compartment 98 to be filled by exudates leaving the wound site as seen in FIG. 16. In this embodiment, the compartment 98 may be suitable for isolating exudates for analysis or to periodically weigh exudates removed from the wound site so as to assess the rate of fluid removed from the wound site over time. The compartment may include an automatic means for emptying when the fluid volume reaches a set level. Alternatively, the compartment may have an active system such as valves 99, to empty the compartment 98 when the fluid 97 reaches a set level. Fluid may enter the compartment 98 through an inflow tube 96, and exit the compartment 98, via an exit tube 103.

In this embodiment, the exudates system may comprise one or more valves 99 to direct and/or interrupt flow through the wound drain. In yet another embodiment, the exudates system may draw off fluid for a sample without fully interrupting flow through the fluid line. The separated fluid as indicated in FIG. 16, is analyzed within the line and allowed to remix further downstream. An alternative design may include a sampling port for taking a sample for analysis.

FIG. 21 depicts another embodiment, in which an exudates system 220 may be implemented as an add-on accessory in a canister, along an inner or outer surface of a canister or arranged so as to mate with a canister. In this embodiment, the exudates system may be arranged to detect the value of exudates accumulated during use as well as monitor exudates properties as previously discussed. In this embodiment, the exudates system may monitor and detect the weight, height, impedance, etc. of the exudates as they accumulate in the canister. Such information may be valuable for determining the overall rate of exudates removal from the wound site, thus providing predictive planning for canister changes or to monitor wound progression from a highly exudating state to a superficially exudating state.

Changes in the rate of exudates flowing from the wound site may be indicative of a change in the wound state. In another instance, changes in the composition of the wound exudates may indicate a clinically relevant change in the wound state. Such changes in exudates removal rates may also be useful in determining how to most optimally change from one therapy to another. In one instance, a relative change from a highly exudating wound to one of a superficially exudating wound may be useful to monitor. A transition from a highly exudating wound to a superficially exudating wound may provide useful information as to when a patient may be transferred from a more expensive to a less expensive therapy. An example of an expensive therapy is NPWT, while examples of lower cost therapies are moist wound dressings or bandages.

The system may also be used on its own, without a wound treatment device. For example, FIG. 1B depicts a wound exudates system 18, with sensors 23 in direct fluid communication with a wound. This embodiment, of the wound exudates system used without a wound therapy device, may be useful for wounds where active and passive therapies are contraindicated.

Figure 9:
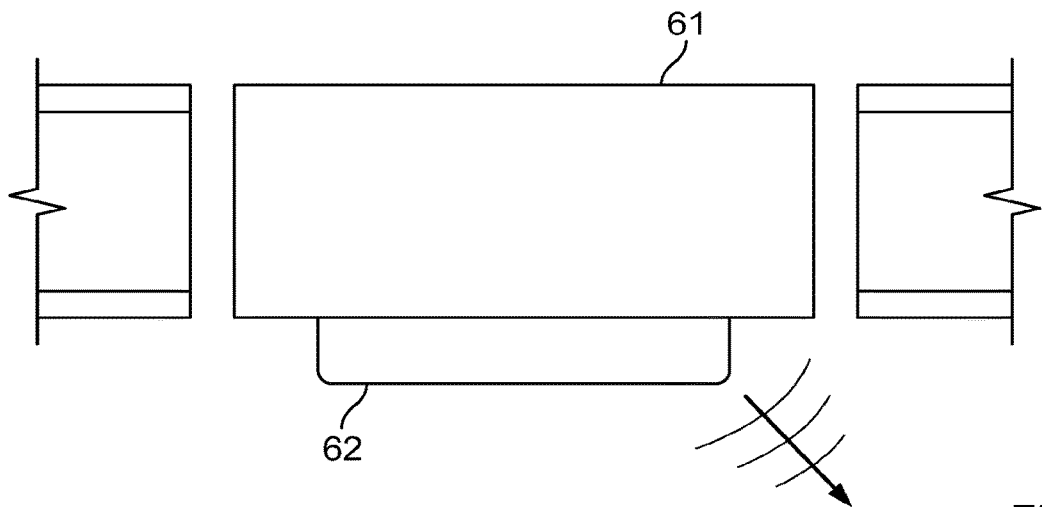
FIG. 9 depicts a wound exudate system that may be inserted into a wound treatment line, in accordance with an embodiment of the present invention.

In an alternative embodiment (FIG. 9), the exudates system may be introduced into an existing NPWT line for example, as a patch, such that exudates may come into direct contact with the system. In this case, the exudates system may have a disposable component 61 and/or a reusable component 62. The disposable component as indicated in FIG. 9 is the tube element that directly couples with the fluid line and comes into contact with the fluid. The reusable component, as seen in FIG. 9, may be the electronics and housing that do not come into direct contact with the wound exudates. It is also possible to design the system such that it is entirely reusable and may be used across multiple dressing sets or even multiple patients.

The exudates system may comprise a sensor or series of sensors suitable for determining the values of the above properties of wound exudates.

The exudates system may comprise one or more disposable sensors for enabling contact based measurements of the exudates. Such sensor elements may comprise acoustic, photoacoustic, electrochemical, optical, and/or impedance spectroscopic elements arranged so as to monitor values of one or more parameters of the exudates.

The sensor or sensors may be arranged so as to collect information through the outer film of a dressing or through the wall of a wound drainage line. The sensors may be temperature sensors, optical sensors, impedance sensor, electrochemical sensors (e.g. amperometric sensors), capacitive sensors, or the like.

The exudates system may comprise any type of flow sensor known in the art for determining the quantity or rate of fluid removed from a wound site. The flow sensor may be of a contact or non-contact type. In the case of a non-contact type flow sensor, the sensor may be a level sensor, a load cell, a flow event timer, a droplet counter, a velocimeter or the like. In the case of a contact type flow sensor, the sensor may be a load cell, pressure head monitor (such as a manometer), a strain gauge, a turbine, a thermal mass sensor, pressure loss monitors, a tow line, or similar.

In one embodiment, the sensor may be a temperature sensor. In this case, the temperature sensor may be arranged so as to mate with the outer film of a dressing or to an outer wall of a wound drainage line. In another embodiment, the temperature sensor may be situated within a disposable tube, the disposable tube being able to be spliced into an existing wound drainage line. In either case, the temperature sensor may be arranged so as to monitor small changes in temperature of the wound exudates.

By combining several sensory sources, a solution may be reached to make reliable and useable quantifications of the state of the wound exudates.

In one embodiment that may be particularly relevant to the clinical setting, an exudates system may include a plurality of sensory systems for measuring values, such as a color analysis system in combination with a volume rate measurement system.

In such an embodiment, several of the above sensory approaches may be combined, so as to provide reliable assessments of the state of the wound, and potential treatment options at a given time.

Any physiological parameter of wound exudates may be assessed using embodiments of the present invention. Particular parameters of interest may include, flow of wound exudates, volume rate, pH, temperature, hemoglobin concentration, color and tone.

Flow Assessment

In one embodiment, the exudates system may evaluate exudates flow rates by measuring the rate at which a collection chamber fills, as seen for example in FIG. 16. This may be achieved by measuring the weight of the chamber in combination with measuring the orientation of the chamber. In an associated embodiment, the chamber may have a valve located near the base of the chamber, oriented so as to drain the fluid into an adjacent reservoir. In this example, the viscosity of the exudates may be evaluated by measuring the rate at which the mass of the chamber changes as it is emptied.

In one embodiment the exudates system may comprise a combination of a load cell with a measurement chamber to measure flow rate and an accelerometer to monitor orientation of the measurement chamber with respect to the vertical axis, as seen in FIG. 16. Combined signals from the sensors may be used to determine the correct flow rate of exudates from the wound site independent of the orientation of the exudates system.

Table 1 depicts various flow rates and their potential clinical indications. By quantifying these flow rates, and assessing them together with the other physiological parameters discussed herein, an accurate prediction of wound health may be obtained.

TABLE 1

| Exudate Volume | Wound State | Clinical Relevance |
|---|---|---|
| Nothing | dry wound | desiccation |
| Scant | moist wound tissue (good) | Normal |
| Somewhat | wet wound tissue | Potential maceration |
| Moderate | saturated wound tissues | Likely maceration |
| Copious | wound tissues are bathed in fluid | maceration |

In one example of the present technology, a collection canister was built to demonstrate flow measurement using the concept illustrated by the embodiment in FIG. 21. FIG. 21 is an alternative embodiment of the present invention depicting a wound exudate system and strain gauges disposed within an ancillary collection chamber. Such measurements may be taken by one or more sensors, including but not limited to strain gauges 236, a capacitive level gauge 244, optical gauge elements 242, and electrical gauge elements 240. Standard types of gauges for measuring weight or level are well known in the art. For example a strain gauge is based on a simple electrical circuit, wherein mechanical stress caused by change in weight causes the electrical resistance of the elements to change in proportion to the weight applied. A capacitance gauge reads a different level of capacitance between two points. In the present technology, the level of fluid 235 in the chamber (e.g., the wound fluid) may have a different value of capacitance to that of air so the level of the fluid in the container may be determined. Alternatively, an optical gauge may use light to determine the distance between two points (e.g., the top of the canister and the fluid may indicate changes in the level of the fluid.

The system 220 in this particular example consisted of a small reservoir 230 in fluid communication with a larger reservoir 232, an inlet port 234 feeding into the small reservoir 230. The small reservoir 230 was attached to the larger reservoir 232 with a flexible support 238. A strain gauge based load cell 236 was applied to the flexible support in order to measure flexure of the support during use 238. Saline was used to approximate the fluid under measurement during the study. The system 220 as also equipped with electrical gauge elements 240, optical gauge elements 242, a capacitive level gauge 244. The example demonstrated, among other things that individually, or if necessary in combination, different sensor types may be used to determine flow rate.

In this example, small amounts of fluid were fed through the inlet and the sensor response was recorded on a computer (PC). During injection of fluid, the reservoir was subjected to chaotic disturbances in an attempt to disrupt the sensor readings. Such inputs would be typical of movements experienced by the device during a mobile use scenario. The response data was filtered using finite impulse response and infinite impulse response filters. The filters were used to remove movement artifacts and recover a usable signal from the input.

In general, the response data signal read into the system was related to the weight of the small reservoir. This is in turn related to the time integral of the flow rate of fluid into the container. Thus the flow rate was able to be extracted from the reservoir weight signal.

A valve 246 was used between the small reservoir and the large reservoir in order to drain and reset the reservoir when it became too full. The flow dynamics of this emptying process can be used to determine viscosity related information about the fluid under study.

Figure 22:
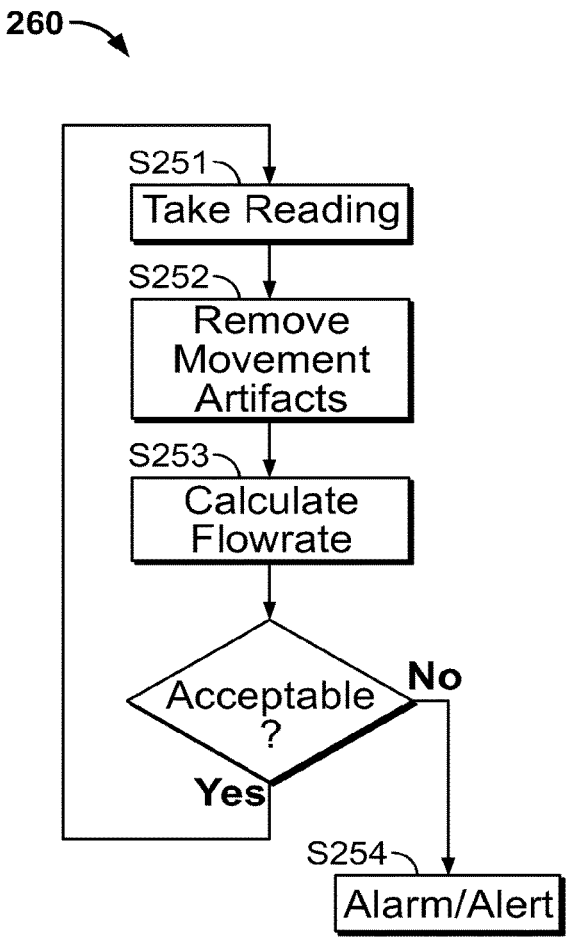
FIG. 22 is a flow diagram illustrating an exemplary process for obtaining flow measurements of wound exudate measurements, in accordance with an embodiment of the present invention.
Figure 23:
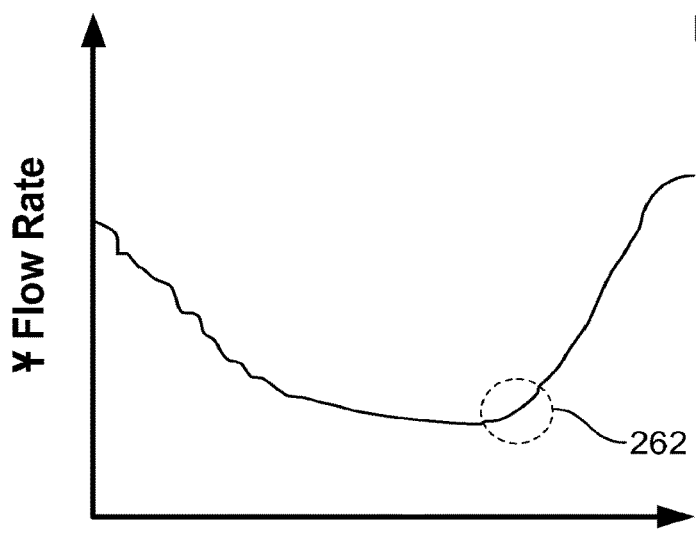
FIG. 23 is a two-dimensional graph depicting flow rate measurements, in accordance with an embodiment of the present invention.

FIG. 22 depicts a process 260 related to flow measurement of FIG. 16 and FIG. 21. The process 260 includes (1) taking a flow reading in block S251; (2) removing any movement artifacts in block S252 (1); and (3) calculating a flow rate in block S253 based on methods known in the art and, in particular, those disclosed herein. If the calculated flow rate is acceptable, measurements will continue to be taken. It the flow rate is not acceptable an alarm or alert is triggered in block S254. The flow rates calculated in process 260 may also be mapped in a graph as seen FIG. 23. As with process 260, the spectral maps showing various values along the flow rate map that may indicate an onset of infection and/or bleeding, i.e. 262.

A valve 246 was used between the small reservoir and the large reservoir in order to drain and reset the reservoir when it became too full. The flow dynamics of this emptying process may be used to determine viscosity related information about the fluid under study.

Exudate flow rate, which may be measured by the methods described herein, or any of the methods known to those of ordinary skill in the art is a reliable predictor of wound health. In certain embodiments of the present invention, flow rate values, and changes in flow rate values may be detected through various means and may also be useful in determining how to most optimally change from one therapy to another. In one instance, a relative change from a highly exudating wound to one of a superficially exudating wound may be useful to monitor. A transition from a highly exudating wound to a superficially exudating wound may provide useful information as to when a patient may be transferred from a more expensive to a less expensive therapy. An example of an expensive therapy is NPWT, while an example of a lower cost therapy is moist wound dressings or bandages. In one instance, changes in the rate of exudates flowing from the wound site may be indicative of a change in the wound state. In another instance, changes in the composition of the wound exudates may indicate a clinically relevant change in the wound state.

In another embodiment, color assessment of a disposable element within the device, or disposable electrodes within tube may be possible. It may also be possible to map color profiles of exudates to pH. Several fluorescent nanoparticles systems may change color based on pH. In addition, a conjugated polymer could be used to do the same (redox potentials will change based on the pH of the local environment).

Additionally, it may be possible to have a color changing element in contact with the exudates that is responsive to local pH changes and a reusable reader element that may analyze the pH changes via monitoring color response of the color changing element.

Temperature may be useful for assessing bleeding events as well as to monitor for infection. Core blood is generally warmer than the interstitial fluids in the dermis. In general, embodiments using a disposable metallic element for measuring temperature values, as well as embodiments with reusable probes are envisaged.

In one aspect of the present invention, near infrared spectroscopy/visible spectroscopy may be used to detect the values of oxygen in hemoglobin present in wound exudates. The presence of oxygen may indicate the presence of hemoglobin, and therefore blood. In aspects of the present invention, this could trigger an indicator, or cause one of the pinch mechanisms described herein to clamp a wound drain line to prevent further bleeding. In yet other embodiments, this event may provide a caregiver with appropriate treatment guidelines.

Tone and/or luminosity are used to describe the color of the exudates. Changes in tone and/or luminosity may be indicative of changes in the physiological state of a wound and its stage of healing. A quantification system for evaluating the wideband absorption spectrum may also be useful for assessing the color and tone of the exudate.

In one embodiment, a wound system may include one or more laser diodes that provide very narrow wavelengths used to perform measurements. In this case a spectral map and/or vector may be generated by using a single detector in combination with multiple laser diodes and/or one or more scanning laser diodes. A scanning laser diode may produce a modulated wavelength through modulation of the driving signals produced by the drive electronics. Such modulation makes for simplified removal of artifacts caused by ambient light interference, movement and the like.

A method for quantitative, real time spectral detection and assessment may be a steady, pulsed or modulated near infrared spectroscopy or functional near infrared spectroscopy technique. It may use multiple wavelength spectroscopy and the like. In one case, a exudates system may include a color analysis system in combination with a white light source. A color analysis system may comprise one or more photodiodes in combination with one or more bandpass filters in order to provide separate responses for segments of the light spectrum. One or more outputs from each band are generated, with each output providing the spectral component of a vector. Output vectors may be mapped to exudates states, thereby creating vector maps useful for determining the state of the exudates and thus, statements about the physiological condition of the wound, as seen in FIGS. 19 and 20.

Figure 17:
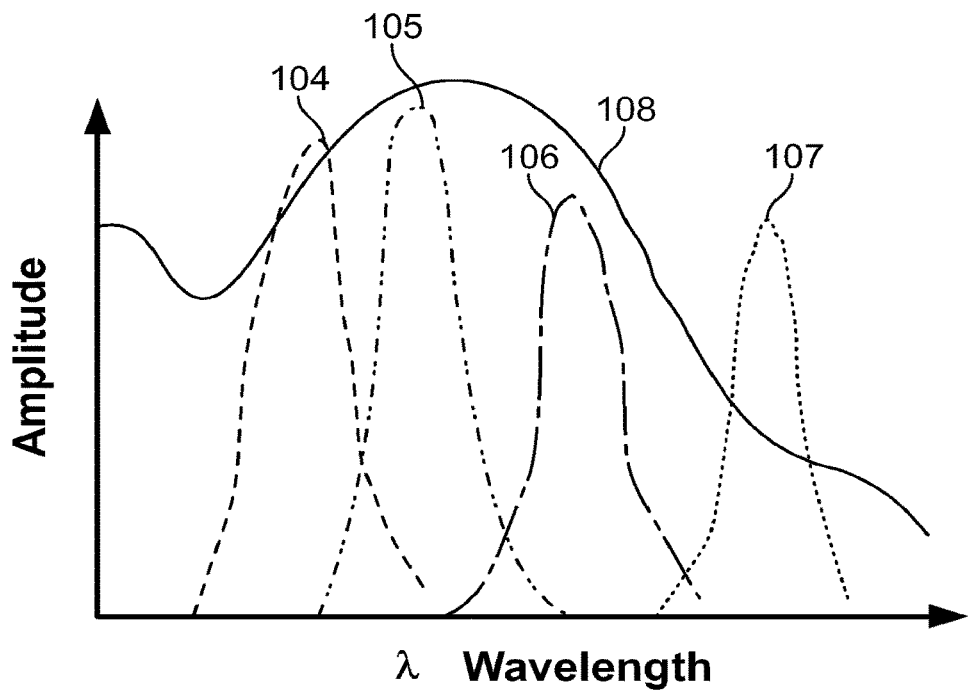
FIG. 17 depicts a graph showing different spectral intensities, in accordance with an embodiment of the present invention.

FIG. 17 is one example of an absorption map or tone map for analyzing different absorption wavelengths. As depicted in FIG. 17, by representative example only, a two-dimensional map shows absorption of a source spectrum 108 along a blue 104, yellow 105, red 106, and NIR 107 wavelength. This particular example depicts broadband detection for the colors indicated. However, in alternative embodiments, a single broadband detector could also be used. Particular values seen in an absorption map may be translated into a particular assessment of a wound state. By way of example only, a process performed by the processor may be encoded to signal an alarm or pinch a drain line if a particular tonal color reaches a certain level.

Figure 18:
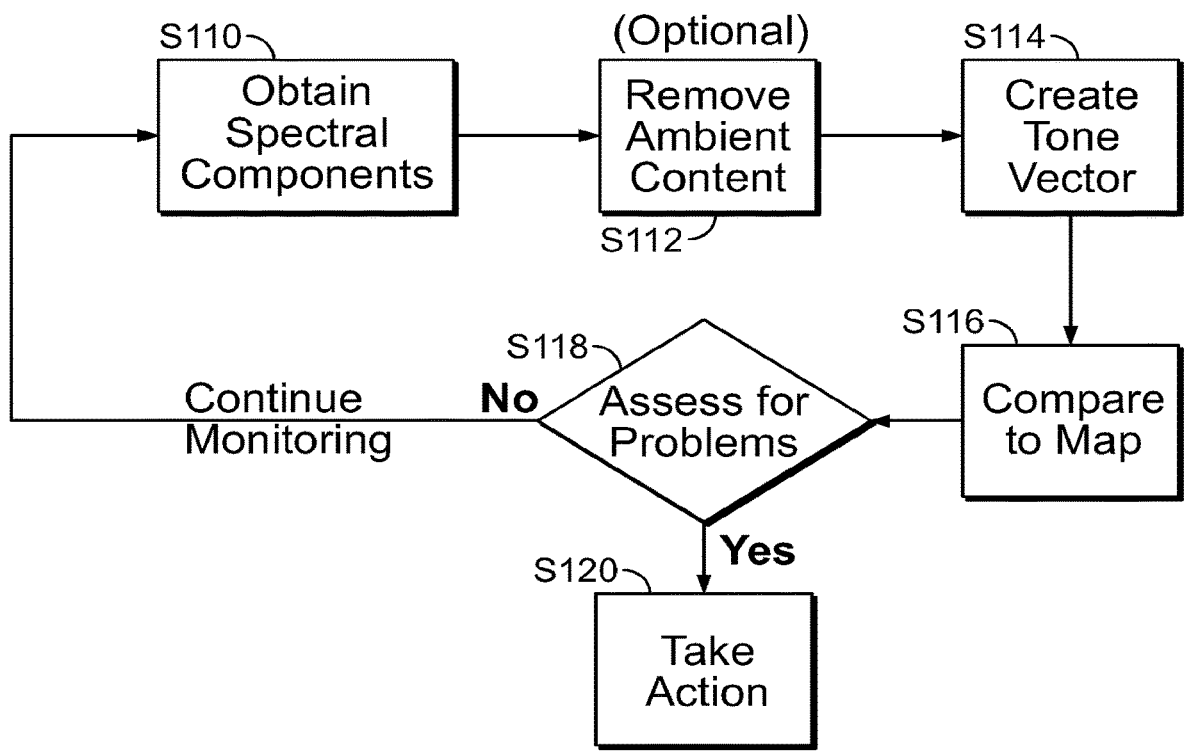
FIG. 18 is a flow diagram of a process for spectral analysis of wound exudate, in accordance with an embodiment of the present invention.

FIG. 18 depicts a flow diagram of various operations performed to assess the color or tonal characteristics of a wound exudate. An initial block S110 may obtain various spectral components. Next, any ambient light may be removed in block S112 to increase the accuracy of any spectral readings from the wound exudate. Once block S112 is completed, tone vectors are calculated in block S114 from the readings obtained from block S110. Tone vectors may be calculated by any means known in the art. However, in preferred embodiments, the vectors may be calculated using the following equation:

$$\delta = \sum_{i=1}^{N} A_i X^i \qquad \text{Equation 1}$$

Equation 1 is a linear weighting equation that casts portions of the sensor spectrum (each portion indicated by a coordinate $X^i$) into an nth order vector space. Each portion of the spectrum is weighted by a scalar weighting parameter $A_i$ (in this example only, more generally the weighting parameters can be equations, etc. that better map responses into the vector space, adjust for subject parameters, as well as adjust for changes in ambient conditions, etc.).

The relationship computed in the equation may be used to map readings from individual sensors, wavelengths, and/or spectral bands into the nth dimensional figures, as disclosed herein. This process is done to essentially create a map of the input responses into a quantifiable space such that diagnostic information may be more readily extracted from the collection of input signals. So for example, delta maps into this nth order space, regions of which may have statistically significant relationships to various disease states, contraindications for the existing therapy, etc. By correlating where patient data falls on the map, and examining the historical data and trending data, the technology can assist in decision making with regards to therapeutic decisions.

These tone vectors are then compared to a tone map block S116 containing standard or acceptable tonal values. In assessing for any potential problems block S118, the tone vectors from block S114 are compared to the accepted values in block S116. If any of those values fall short of or exceed the acceptable ranges from block S116, a predetermined action in block S120 is performed. A programmed action may include, triggering an audible alarm from actuating one of the latch mechanisms described herein.

In particular, luminosity and tone may be indicative of infection, bleeding or increased edema in a wound, all conditions requiring urgent attention. Certain embodiments of the present invention may compare and analyze detected tone and luminosity values with predetermined values of tone and luminosity to provide a patient or caregiver with valuable treatment guidelines (see FIGS. 19A, 19B and 20). Values of these various parameters may be combined into vector maps.

Figure 19A:
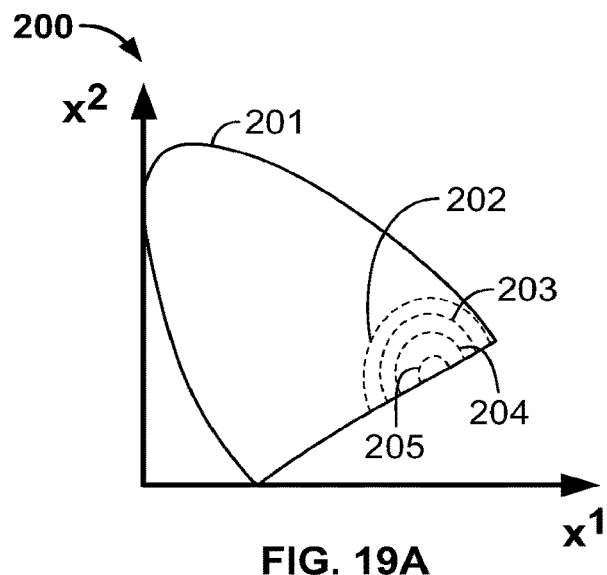
FIG. 19A is an exemplary two-dimensional vector map representing a range of wavelengths measured during spectral analysis of wound exudate, in accordance with an embodiment the present invention.
Figure 19B:
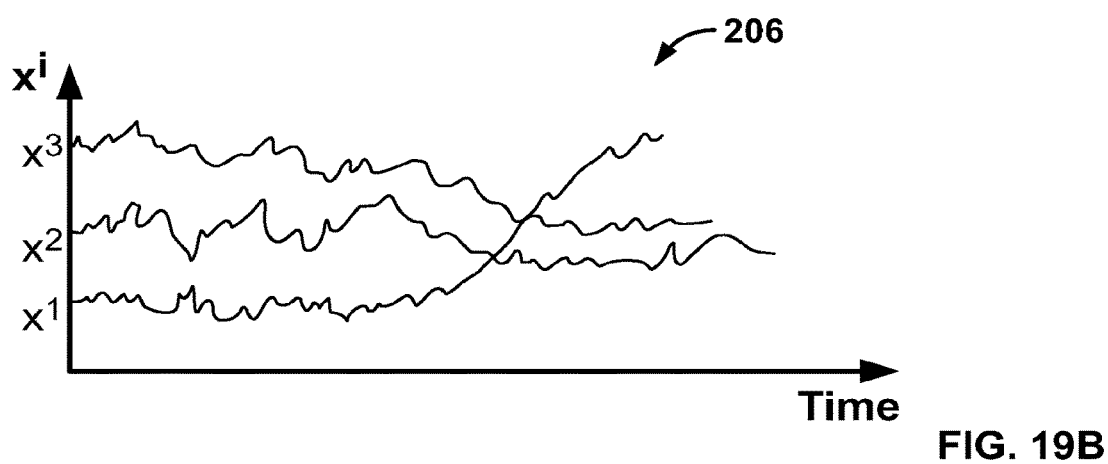
FIG. 19B is a spectral graph of the measurements of the map of FIG. 19A, in accordance with an embodiment of the present invention.
Figure 20:
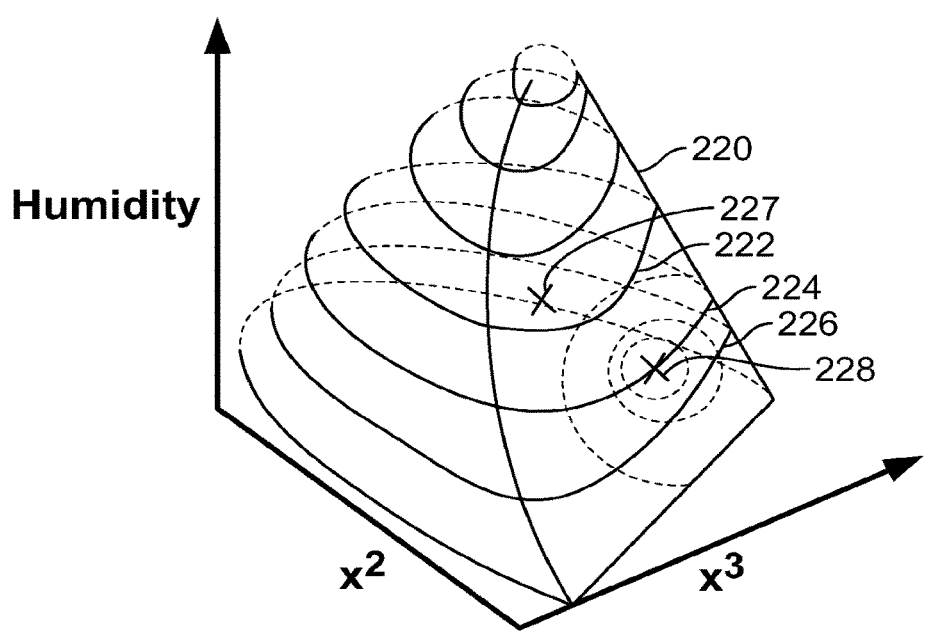
FIG. 20 is an exemplary three-dimensional vector map representing a range of wavelengths measured during spectral analysis of wound exudate, in accordance with an embodiment of the present invention.

FIG. 19A is a two-dimensional vector map 200 based on a range of colors at a given luminosity 201, measured from the wound exudate. Map 200 represents data points along the spectral graph 206, as shown in FIG. 19B. Different locations on the vector map 200 may indicate the likelihood or actual occurrence of various events related to wound state. For example at location 202 a normal exudate trend may be indicated, while locations 203 and 204 may indicate suspected bleeding or a high probability of bleeding, respectively. Location 205 may indicate the presence of an actual bleeding event. Graph 206 represents a line graph of three individual spectral profiles over a given period of time.

FIG. 20 is a three-dimensional vector map, similar to the two-dimensional map shown in FIG. 19, which is based on a range of colors measured from the wound exudate. Spectral components of wound exudate translated into vectors, may be mapped in such a two or three-dimensional map. By increasing the number of color channels, and therefore the number of wavelengths able to be detected, the sensitivity and accuracy of the system may be improved. Various points along the vector map, whether two or three-dimensional, may also indicate a trend of wound health. For example curve 220 may indicate an initial trend while curve 222 may indicate a slight progression towards infection. Curve 224 may indicate the actual onset of infection while curve 226 may indicate various regions with a probability of infection.

Given points, such as 227 and 228 in the vector map may indicate a certain wound state. Such a wound state may correspond to a prescribed treatment guideline. These treatment guidelines may include, but are not limited to varying the settings of an NPWT, or closing off a wound drain. Presence of bacteria or other infection may necessitate administration of antibiotics to the patient.

Qualitative analysis of the color spectrum of wound exudates may be another valuable tool for assessing wound health. Table 2 depicts various exudates, their color, transparency and possible clinical indications.

TABLE 2

| Type of Exudate | Color, Transparency | Viscosity | Indications |
| --- | --- | --- | --- |
| Serous-transudate | clear, straw colored, | low viscosity, watery | normal (good) |
| Fibrinous | cloudy | low viscosity, strands | contains fibrin |
| Sero-sanguinous | clear, pink | low viscosity, watery | normal (good) |
| Sanguinous | red | low viscosity and watery | blood vessel trauma |
| Sero-purulent | murky yellow to creamy coffee | high viscosity | infection |
| Purulent | yellow, grey, green | high viscosity | presence of inflammatory cells, infection, pyogenic organisms |

TABLE 2-continued

| Type of Exudate | Color, Transparency | Viscosity | Indications |
| --- | --- | --- | --- |
| Hemo-purulent | Dark, red, | high viscosity and sticky | established infection, presence of neutrophils, bacteria, inflammatory cells with blood leakage due to vessel damage |
| Hemorrhagic | Red | thick | infection with trauma |

Practically, when considering diagnostic and treatment options for a patient suffering from a wound, in general, a clinician does not want to be inundated with data. It is desirable that an exudate assessment system analyze values detected from a wound, and provide decision support for the user regarding treatment options, rather than just data presentation. To that end, the system of the present invention may be capable of analyzing the values of the data obtained from the sensors and/or detectors. Once an analysis is conducted the system may provide an assessment of the wound, as well as treatment guidelines.

Figure 24:
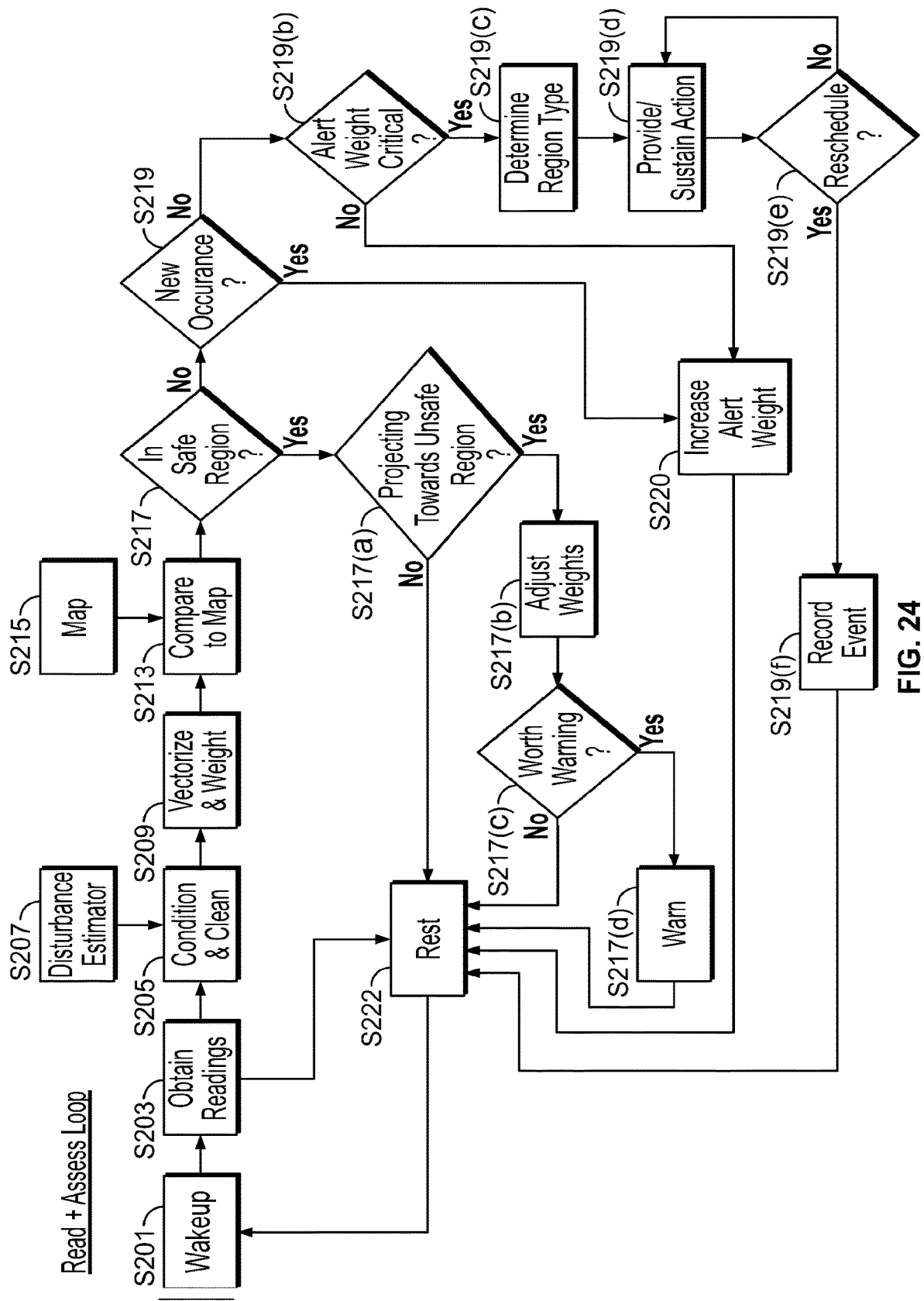
FIG. 24 is a flow diagram illustrating the steps in a read and assess loop process, in accordance with an embodiment of the present invention.
Figure 25:
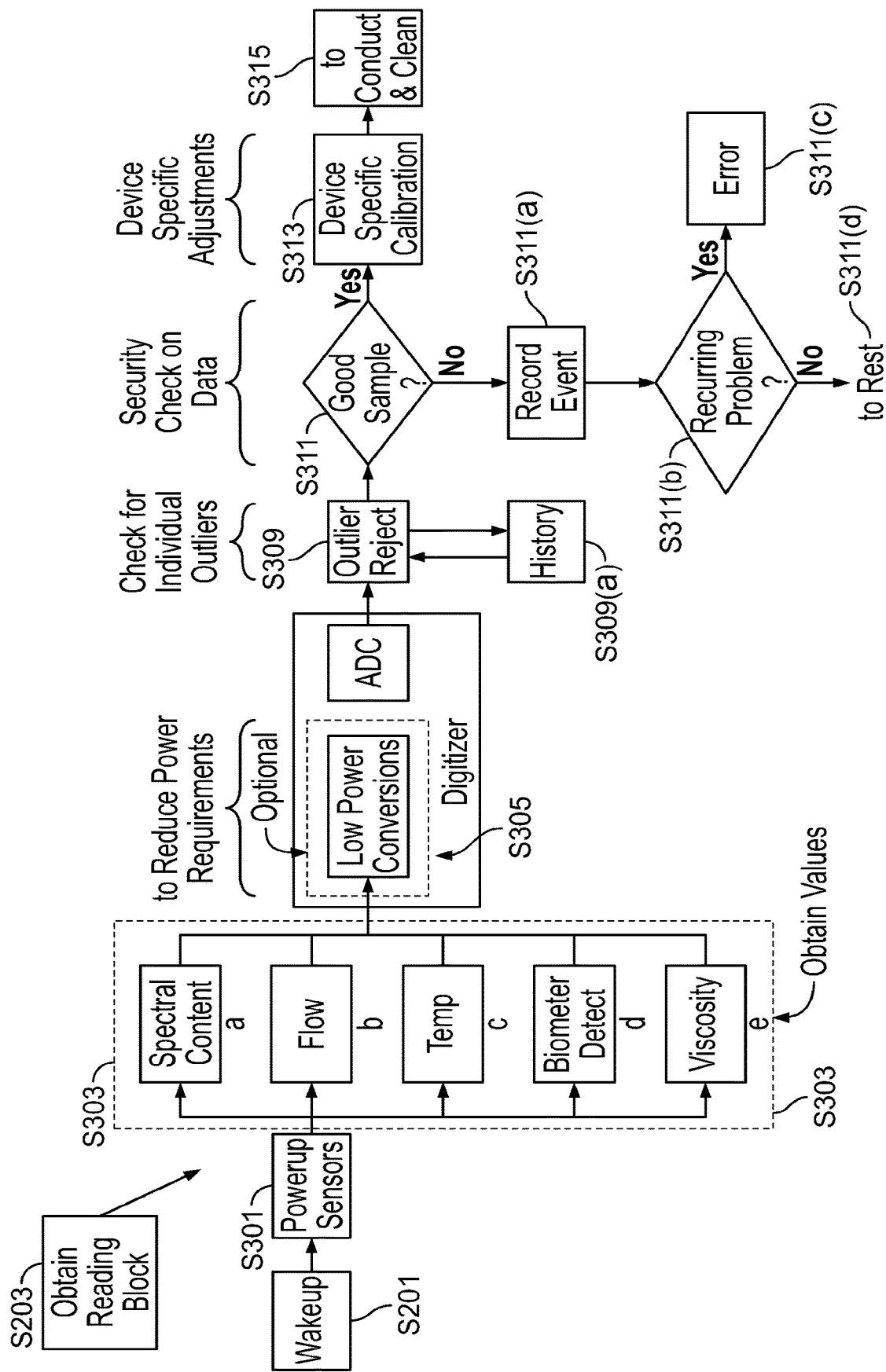
FIG. 25 is a flow diagram illustrating a process for obtaining readings of wound exudate, in accordance with an embodiment of the present invention.

Embodiments of methods and apparatuses according to the present invention may detect values of various parameters in real time, and perform analyzing processes as shown in FIGS. 24 and 25. These analyzing process provide not only real time detection, which gives a much more accurate and reliable assessment of the wound, but also gives real time treatment suggestions, as they evaluate the current state of a wound, and not exudate that has been sitting in a collection canister for an extended period of time.

The exudates system may comprise processing components to perform various processes that provide or output a wound state condition or treatment option, which may include, among other things, microelectronic circuits such as discrete circuits, microcontrollers, microprocessors, ASICs, FPGAs or the like, to condition and analyze sensor data to meaningfully interpret the physiological parameters of the exudates. The processing components may be located integrally within the system so that the sensors, light sources and processing components are all contained within the same device. In an alternative embodiment, the processing components may be remotely located from the other parts of the system.

The process performed for analysis are generally adaptive and may be based on, one or more of the following: an averaged one-dependence estimators (AODE), Kalman filters, Markov models, back propagation artificial neural networks, Baysian networks, basis functions, support vector machines, k-nearest neighbors algorithms, case-based reasoning, decision trees, Gaussian process regression, information fuzzy networks, regression analysis, self-organizing maps, logistic regression, time series models such as autoregression models, moving average models, autoregressive integrated moving average models, classification and regression trees, multivariate adaptive regression splines.

The sensor data may be analyzed from multiple sources using sensor fusion approaches. The specific process may be evolved using supervised learning, unsupervised learning, and/or reinforcement learning approaches. In addition, the device may comprise associated power sources and the like to drive the onboard electronics (sensors, microelectronic circuits, communication elements).

When tone and luminosity values are analyzed in combination with temperature readings, flow rate and NIR readings, a comprehensive statement may be made about the actual state of the exudates. By applying the processes described above to the various physiological parameters, including tone, luminosity, temperature and flow, a clinically appropriate set of treatment guidelines may be delivered by the system, thus eliminating the need for the caregiver or patient to have to interpret large amounts of data and make a subjective determination.

FIG. 24 is a flow diagram of an exemplary process to obtain and analyze parameter readings, as well as present and display warnings and treatment options.

The process of FIG. 24 is also referred to as a read and assess loop. The system may be at a sleep state to reserve or reduce power consumption. The system may be "woken up" during a wake-up phase S201, in response to some input. This input may be any type of stimuli such as motion, or as a result of a timer. Once awake, the system will obtain parameter readings S203. After block S203, the device may immediately return to a rest state in block S222. If this is the logic path followed by the device, the readings obtained in block S203 may also be stored in a memory.

If after obtaining readings in block S203, the system does not immediately return to rest S222, the device may be conditioned and cleaned in block S205. This cleaning step aids in obtaining an accurate reading and filtering out any extraneous data or artifacts. In the first mode from wake up, the device may be in a loop where it simply wakes up, takes a reading, potentially stores it and then rests, as already described. If instead of resetting, the device needs to switch modes to monitoring disturbances from block 207 it will need to activate a conditioning function, which may be there to obtain the raw signals from 207 and prepare them for analysis (e.g., converting from analog to digital signals depending on sensor type or other forms of data conversion/signal conditioning know in the art). It may also be necessary to clean the signals because many signals can have "noise" or spurious data which need to be filtered out before processing in 209.

After blocks S205 the readings obtained in step S203 are converted to vectors and assigned a corresponding weight S209. The weighting of the various readings may be based on any factor known in the art. By way of representative example only, one parameter such as temperature may be given a higher weight than pH, or vice versa. Such weighting may be changed from patient to patient or as applied to the same patient. Such weighting may also be assigned based on historical weights of various parameters 211. Once the readings are vectorized and weighted, the processor in block S213 compares the vectorized and weighted values to a vector map. At this point, the processor analyzes the data, and makes a determination, based on the vector's location on a vector map, as to whether the value is in a safe region in block S217. What constitutes a safe region is also a parameter that may be predetermined and stored in a memory associated with the processor. If, it is determined in block S217A the readings are in a safe region but appear to be trending toward an unsafe region, the weights of those readings may be adjusted in block S21/(b) to assign a higher priority to said values. Next, based on the adjusted weights, the system makes a determination as to whether or not it is worth warning a user S217(c) of the trend toward an unsafe region. If based on predetermined values, the processor determines that it is in fact worth warning a user, then a warning is issued in block S217(d). If not the system returns to the rest state 222 for power minimizing consumption.

If the vectorized and weighted reading is not in a safe region, the processor in block S219 determines whether or not the unsafe reading is a new occurrence S219. If it is a new occurrence, the alert weight of the occurrence is increased in block S220. Once the alert weight is increased, the processor returns to the rest state S222. If the device or processor determines that the unsafe reading is not a new occurrence, a determination is made by the processor in block as to whether the alert weight is critical in block S219(b).

If the alert weight is not critical, then the alert weight is merely increased in block S220 and the device returns to rest state S222. If the alert weight is critical, the processor determines in block S219(c) which region of the vector map the value falls in and what type of condition is therefore indicated by the value of the readings. Based on the region and type of event detected at in block S219(c), an action is initiated in block S219(d). An action may be an alert, an alarm, a pinching of a wound drain, or any other type of event or warning, which aids the user in assessing or treating the wound. If the action taken at block S219(d) is resolved, as determined in block S219(e) the device and/or processor will record the event in block S219(f) and return to rest S222. If the event has not been resolved, the action at block S219(d) will be repeated or sustained.

At block S203 at the read and assess loop, readings are obtained. FIG. 25 is a detail logic diagram of operations performed in block S203. Once the processor or device "wakes up," the sensors are powered up S301. Once the sensors are powered up, parameter values may be obtained S303. As depicted in FIG. 25, parameters such as spectral content of the wound exudate S303(a), flow S303(b), temperature S303(c), biomarker detection S303(d), and viscosity (e) are detected and measured. While these parameters are illustrated in FIG. 25, they are by way of representative example only and the current invention may be used to measure any parameter present in wound exudate. These values are then converted to digital signals in block S305, which may be done as a low power conversion to reduce power requirements. Once the values have been digitized, the processor in block S309 performs a check for values that may be statistical outliers. At block S309, as part of the outlier analysis, the values may be stored in a memory to be incorporated into the historical data S309(a). If the sample is determined to be a good sample in block S311, the processor will perform a specific calibration S313 to adjust to the specific present conditions.

Once this adjustment is performed, the processor in block S315 may perform the conditioning and cleaning similarly as in step S207. If the sample is determined by the processor in S311 to not be a good sample, the event is recorded in block S311(a). If the bad sample is a recurring problem, which may be detected by prior historical values, an error message is displayed to the user in block 311(c). If the problem sample is not recurring, the processor returns to rest S311(d).

For example, after the processor has determined the wound state and/or treatment information, that data may be provided or communicated to a user or patient. As discussed above, the system is capable of communicating or providing values and treatment guidelines to a user. In addition, the system is also capable of communication directly with a negative pressure wound therapy device in order to effectuate necessary changes.

The system comprises means for alerting a patient or caregiver to the presence of an abnormal state, quantity, or condition of the exudates. In this case, it may comprise one or more lights, a display, a speaker, a vibrating element, or similar in order to communicate information to a patient or caregiver.

The device may further include wireless communication capabilities so as to deliver relevant information about the wound exudates to the NPWT device. Such information may include the presence of blood in the exudates, the presence of bacteria, a change in the absorption spectrum of the exudates, a change in the flow rate of the exudates, and the like.

Results of the wound assessment may be displayed through any type of graphical user interface, monitor or other type of display. Results of wound assessment may also be conveyed to a clinician and/or patient by the use of indicators as seen in FIG. 2. Indicators 27 may be visual indicators such as lights, or audible indicators such as buzzers or alarms, or a haptic communication device such as a vibration motor to alert the clinician or patient when a particular event has been detected.

The exudates system may comprise a means for communicating via a network such a cellular network, a wireless personal area network (WPAN), wide area network (WAN), metropolitan area network (MAN), local area network (LAN), campus area network (CAN), virtual private network (VPN), internet, intranet or near-me area network (NAN).

The exudates system may be arranged as a node in a network, thus providing an element in a ring, mesh star, fully connected, line, tree or bus network topology. In one embodiment the exudates system communicates relevant values and as a node in a mesh or star network topology.

The exudates system may comprise means for interfacing with a local telecommunications network, such as a cellular network via a locally positioned mobile handset, a wireless node, a wireless modem, phone adaptor or the like.

The exudates system may communicate relevant information through the network using various protocols such as IrDA, Bluetooth, UWB, Z-WAVE, ANT, or ZigBee. Preferably, the relevant information is sent via low power protocols such as Blue tooth low energy, ANT or ZigBee.

The exudates system may comprise an integrated power switch such that power is automatically provided to the onboard microcircuitry as soon as the system, or a wound device with which the system is associated, is positioned so as to effectively assess exudates. In another embodiment, the system may comprise a proximity sensor to awaken the system itself or wound device from sleep. The sleep function may be useful to reserve power during periods of nonuse.

In another embodiment, the system may include a wound dressing with fluorescent biomarkers as shown in FIG. 8. Biomarkers 50 may be employed for detecting various conditions. Biomarkers 50 may be assessed by externally positioned optical sensors 52, thus providing a non-contact way to assess exudates properties. The optical sensors 52 may use colorimetric analyses to read the biomarkers 50 and detect the presence, absence or quantity of a particular value of a physiological parameter. In one embodiment, an optional light source 56 may be used to emit light into the wound exudate. In this particular embodiment, optical sensors 52 may be located on the outer surface of an opaque, or optically transparent tube 54. Biomarkers may change based on local pH, local impedance, local redox potentials, color, and may fluoresce based on certain criteria, all of which are known in the art. As they interact with the exudates they are useful to detect the presence or absence of certain biological materials. The exudates system may read, detect or assess the biomarkers through optical means (color change, fluorescence, etc.), or electrical means (pH, redox, impedance, etc.).

In yet another embodiment, the system may detect presence of an infection, including but not limited to methicillin resistant *Staphylococcus aureus* (MRSA) or vancomycin resistant enterococci (VRE), to alert a patient at home that they need in-patient hospital treatment. These various infections may be detected by assessing biomarkers integrated within the system, or by assessing the value of other physiological parameters, including but not limited to temperature.

In one preferred embodiment, each process performed by the system may be done in a non-contact fashion such that the sensors and electronics supporting the sensors do not come into contact with the exudates. This allows the components of the system to be reused, as cross contamination is avoided, thus sparing the expense of having to use replaceable sensors with each use.

Figure 15A:
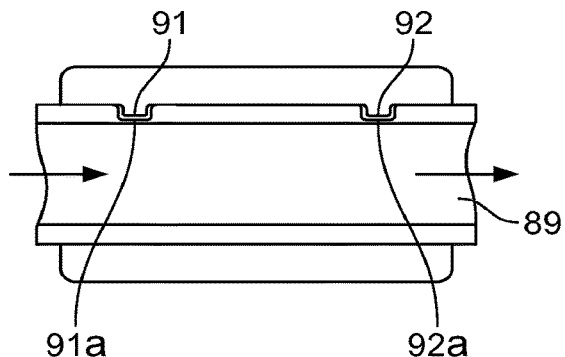
FIG. 15A depicts an embodiment of a wound exudate system containing thin membranes with pressure sensors disposed thereon, in accordance with an embodiment of the present invention.

Non-contact is defined herein as not having direct contact between the fluid under analysis, and the sensory elements. Thin membranes in the drainage lines may be used to sense pressure, temperature, etc. (see FIG. 15). FIG. 15A depicts an alternative embodiment of a wound exudate system, which contains pressure sensors. In the present embodiment, the wound exudate system may contain two sections adjacent to a wound drain 89. Those two regions are indicated in FIG. 15 as 91 and 92 at the interface of the system and the drain where the wall thickness of the system is reduced. At the precise interface between the system and the wound drain, a thin membrane is disposed thereon (not shown). The thinner membrane allows pressure sensors to detect a pressure inside the drain at locations 91a and 92a. A pressure P1 is assigned to a pressure reading at location 91a and a second pressure P2 is obtained for the pressure reading at location 92a. The difference between these two pressure readings may be used to establish, for example, flow rate, viscosity. The configuration described above may be self-contained within a disposable shunt for placement over an existing wound drain line, or designed as an integral component of a wound drain line.

Figure 15B:
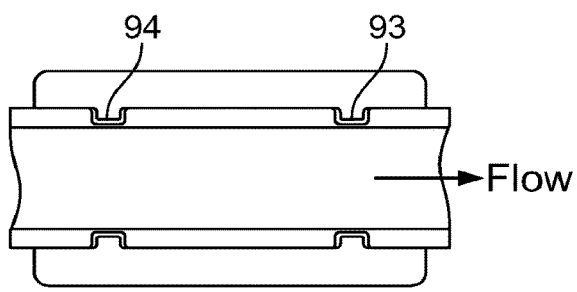
FIG. 15B depicts a wound exudate system containing thermal mass sensors, in accordance with an embodiment of the present invention.

FIG. 15b depicts an embodiment similar to that as seen in FIG. 15a. However, the embodiment depicted in FIG. 15b measures thermal mass vis-à-vis a microheating element disposed in each of recesses 93 and 94. This embodiment may be useful to estimate flow rates along the wall of a wound drain line.

The exudates system may comprise a means for pinching off, or otherwise closing a wound drainage line in the event of an anomaly (such as the presence of blood in the exudates). In this case, the device may comprise an actuator that may be deployed so as to squeeze the line during an adverse event. In another case, the actuator may be arranged such that it is forcefully retracted during normal operation and is released during an adverse event, thus clamping down onto a wound drain line and pinching off fluid flow.

FIGS. 10-14 depict various control mechanisms for controlling or stopping the flow of any fluid from a wound. These control mechanisms may include pinch lines to control the flow of exudates upon detection of a certain physiological value. These pinch mechanisms may also be referred to herein as latches. Different types of latches may be activated by different mechanisms. In one mechanism, the latch is an active material element that will change shape in response to a stimulus. Suitable active materials include shape memory alloys, electroactive polymers, piezoceramics, etc.

In this particular embodiment, the active material latch is designed such that it releases upon stimulation.

If used as part of an NPWT system in response to a certain parameter value, the system may pinch the wound drainage line so as to force a fault (blocked line fault) on the NPWT device. In this case, the system need not have its own means for alerting the patient or caregiver of an adverse event, but rather may trigger an alarm that is present in existing NPWT devices to achieve this goal.

Figure 14A:
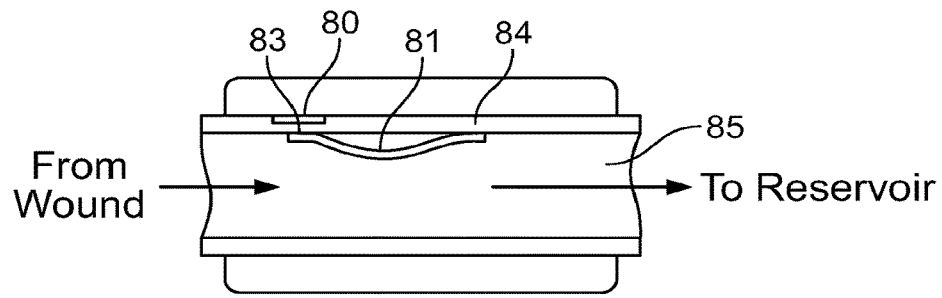
FIGS. 14A and 14B depict a wound exudate system configured with a resistive heat break element in a not applied state, and an applied state respectively, in accordance with an embodiment of the present invention.
Figure 14B:
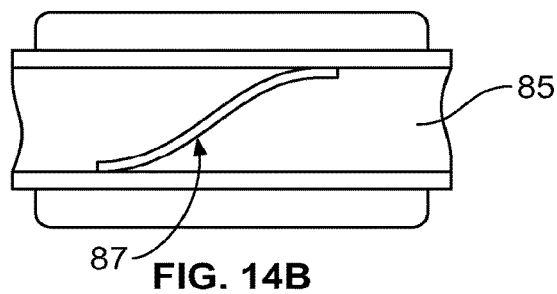

In another embodiment, a suitable latch is designed with an integrated resistive heating element 80, a reed 81 and a disbondable fastened region 83, as seen in FIG. 14A. The reed is deformed during manufacturing and bonded with the disbondable fastened region 83 in the deformed state. The reed is also bonded to an attachment point 84, in which the bond is not broken. The latch system is designed such that fluid may flow through an adjacent channel when the reed is held to the disbondable region, but that fluid flow through the channel on fluid line 85 may be blocked when the reed is released 87. Upon heating of the heating element 80, the disbondable fastened region 83 melts, deforms, or vaporizes, causing the deformed reed to break away from the fastened region 83. During this process, the reed bridges the fluid line 85, as shown in FIG. 14B, preventing flow and optionally triggering a blockage alarm. Other alternative latch designs will be evident to someone skilled in the art.

The wound drain may have a particular shape so as to maintain laminar flow of the exudate during suction, in addition to providing for an actuating means for pinching off a wound drain line in the event of an adverse event such as bleeding. Representative examples of this embodiment may be seen in FIGS. 10A and 10B. The mechanical elements present in this embodiment are comprised of a solenoid based pinch valve 65. As with traditional solenoid based apparatuses, the pinched valve 65 of the present embodiment contains a coil magnet 66 and a coiled actuator magnet 67. In the present embodiment, the pinched valve may be actuated to close or substantially narrow the interior wall of the wound drain 69.

Figure 10A:
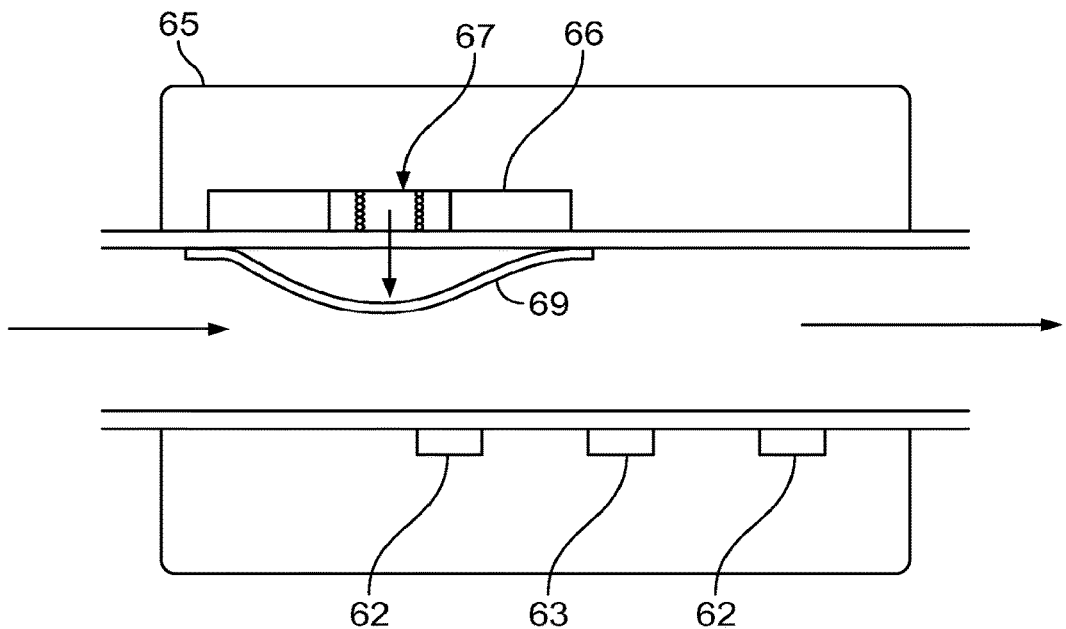
FIGS. 10A and 10B depict embodiments of a wound exudate system for pinching a wound drainage line, in accordance with an embodiment of the present invention.
Figure 10B:
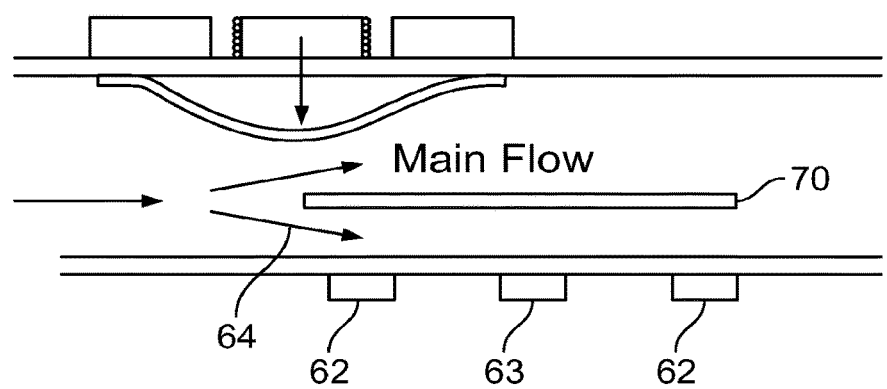

This change of the channel width of the wound drain assists in detecting laminar to turbulent flow and may restrict flow for better analysis or measurement. The embodiment depicted in FIG. 10A may be combined with any of the other embodiments described herein, such as a flow disruption element 70 as shown in FIG. 10B. When flow disruption element is present, analysis and detection may take place along an analysis flow region 64 by sources 62 and detectors 63.

Figure 11:
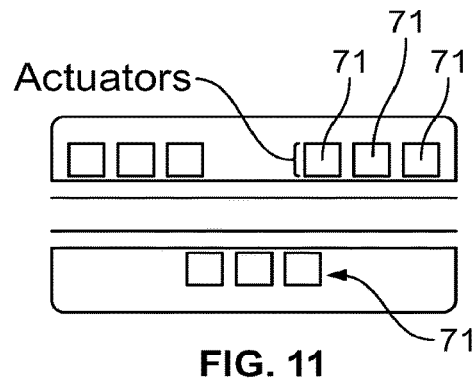
FIG. 11 depicts a wound exudate system with multiple actuators for pinching a wound drain line, in accordance with an embodiment of the present invention.
Figure 12:
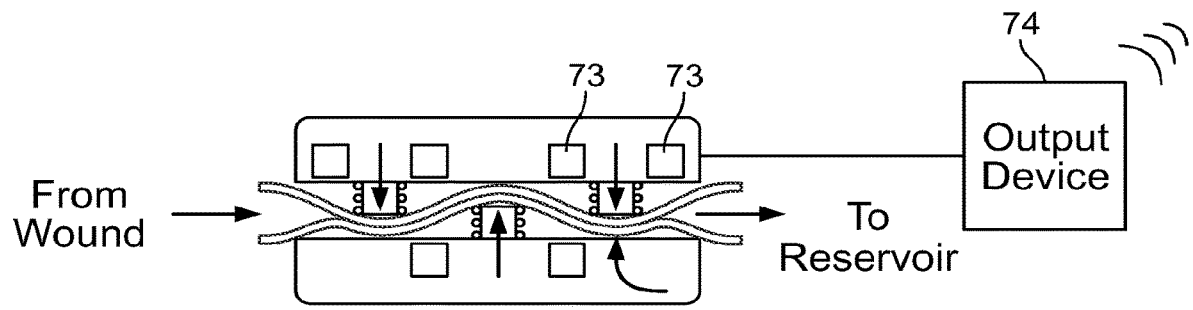
FIG. 12 depicts an alternative embodiment of a wound exudate system having multiple pinching mechanisms disposed along opposing sides of a wound drain line, in accordance with an embodiment of the present invention.

As seen in FIG. 11, more than one solenoid 71 actuator may be used to enhance the pinching affect. FIG. 12 depicts an alternative embodiment wherein multiple pinching actuators 73 are disposed on opposite sides of a wound drain line. The actuators 73, depicted in FIG. 12 may be activated in response to a stimulus, such as the presence of blood. In the event the actuators 73 are activated and pinch the drain line to prevent further bleeding. An alarm may signal a blocked flow line.

Figure 13A:
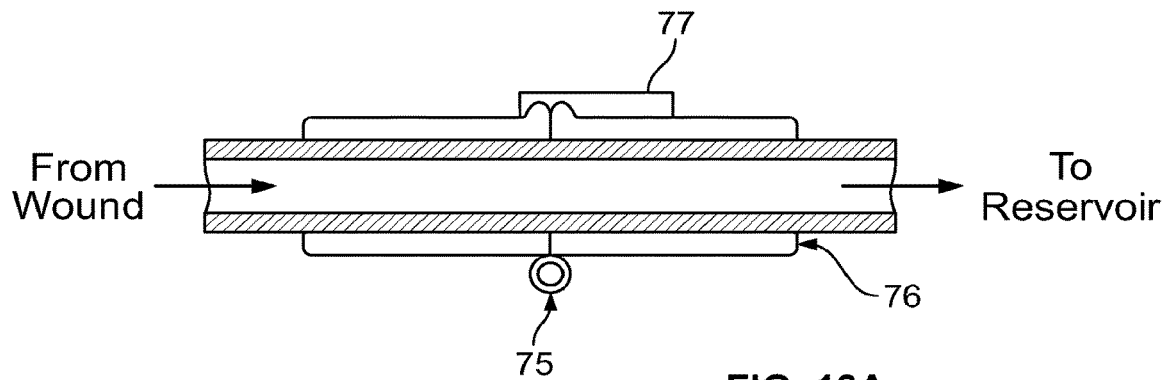
FIGS. 13A and 13B depict an alternate embodiment of a wound exudate system containing a spring loaded latch in a secured state and released state, respectively, in accordance with an embodiment of the present invention.
Figure 13B:
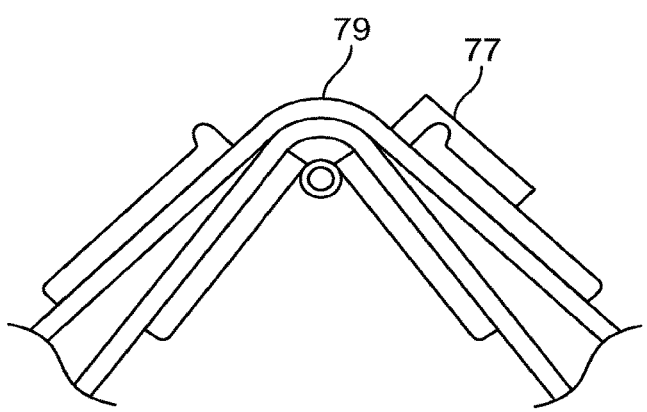

FIG. 13 depicts yet another embodiment of the present invention containing a spring loaded, resettable latch. Upon actuation, the spring loaded latch releases and causes the mechanism to pinch the wound drain line 79 in the event of the detection of some unwanted occurrence, such as bleeding, as shown in FIG. 13B. The spring loaded element 75 once actuated may be reset and the latch 77 may be re-secured, as shown in FIG. 13A. In this particular embodiment, electronics and power sources necessary for operation may be contained on an external housing.

In the case of a conventional dressing or bandage, the dressing component may be modified so as to easily integrate with the exudate assessment system. To enable this integration, the dressing may have electrical traces as an interface. The electrical traces may be printed using electroconductive inks (Ag, AgCl, C, Ni, etc.), or formed via several available RFID techniques known in the art, and embedded for electrically interacting with the exudate assessment system.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A stand-alone system for assessing wound exudate from a wound of a patient, said system comprising:
    a sensor or detector for detecting one or more physiological values of the wound exudate from the wound of the patient;
    a processor for comparing the one or more detected physiological values to one or more predetermined physiological values to obtain a comparison result in real time, and for providing an electronic signal based on the comparison result, in which the electronic signal corresponds to guidelines for treating the wound;
    a compartment for receiving wound exudate from the wound of the patient;
    an exit tube, wherein the compartment is connected to the exit tube;
    a valve positioned relative to the exit tube to control removal of wound exudate from the compartment via the exit tube when the wound exudate reaches a set level in the compartment;
    a reservoir for receiving the removed wound exudate from the exit tube; and
    a transmitter to output the electronic signal for reception by a negative pressure wound therapy device which controls a flow of the wound exudate from the wound of the patient;
    wherein the sensor or detector is positioned on an exterior of the exit tube.

2. The system of claim 1, further comprising a flow disruption element for controlling a flow of wound exudate from the wound of the patient using the electronic signal, in which the flow disruption element is integrally arranged in the system.

3. The system of claim 1, wherein the exit tube comprises an obstruction.

4. The system of claim 1, further comprising an attachment element for attaching to a negative pressure wound therapy device and for enabling the one or more physiological values of the wound exudate to be detected while the negative pressure wound therapy device is in use.

5. The system of claim 1, in which the one or more physiological values include values of tone, volume, thermal mass, flow rate, or viscosity.

6. The system of claim 1, further comprising a memory containing the one or more predetermined physiological values.

7. The system of claim 6, in which the one or more predetermined physiological values are representative of previously obtained physiological values.

8. The system of claim 1, wherein the sensor or detector is positioned to detect wound exudate within the compartment and/or as the wound exudate is removed from the compartment.

9. The system of claim 1, wherein the sensor or detector is positioned on an exterior of the compartment.

10. The system of claim 1, wherein the valve is structured to empty the compartment of wound exudate in response to the wound exudate reaching the set level in the compartment.

11. A stand-alone system for assessing wound exudate from a wound of a patient, said system comprising:
- a wound treatment device comprising
  - a compartment for receiving wound exudate from the wound of the patient, wherein the compartment comprises or is connected to a port or exit tube, and
  - a valve positioned relative to the port or exit tube to control removal of wound exudate from the compartment via the port or exit tube when the wound exudate reaches a set level in the compartment;
- a reservoir for receiving the removed wound exudate;
- a sensor or detector structured to detect or sense a viscosity of the wound exudate;
- a processor configured to analyze the viscosity so as to obtain an assessment of the wound exudate and provide a treatment guideline based on the assessment; and
- a transmitter to output an electronic signal for reception by a negative pressure wound therapy device which controls a flow of the wound exudate from the wound of the patient;
- in which the sensor or detector attach to the wound treatment device.

12. The system of claim 11, wherein the sensor or detector is positioned downstream of an obstruction that disturbs flow of the exudate.

13. The system of claim 11, wherein the sensor or detector is positioned between the valve and the reservoir.

14. The system of claim 11, wherein the valve is structured to empty the compartment when the exudate reaches the set level.

15. A system for assessing wound exudate from a wound of a patient, the system comprising:
- a compartment structured to receive wound exudate from the wound of the patient;
- a valve structured to permit the compartment to fill with wound exudate to a predetermined level, and to empty the compartment of wound exudate in response to the wound exudate reaching the predetermined level within the compartment;
- a reservoir connected with the compartment via the valve such that the compartment receives wound exudate emptied from the compartment;
- a sensor configured to sense one or more physiological values of the wound exudate; and
- a processor configured to compare the one or more sensed physiological values to one or more predetermined physiological values to obtain a comparison result in real time, to determine guidelines for treating the wound based on the comparison result, and to provide an electronic signal corresponding to the guidelines for treating the wound; and
- a transmitter structured to output the electronic signal generated by the processor for reception by a negative pressure wound therapy device that controls a flow of the wound exudate from the wound of the patient.

16. The system of claim 15, wherein the compartment is connected with the reservoir via a fluid line, and wherein the sensor is positioned on the fluid line.

17. The system of claim 16, wherein the fluid line comprises an obstruction, and wherein the sensor is positioned downstream of the obstruction.

18. The system of claim 17, wherein an additional sensor is positioned upstream of the obstruction.

19. The system of claim 16, wherein the sensor is positioned on an exterior of the fluid line such that the sensor does not contact exudate within the fluid line.

20. The system of claim 15, wherein the processor is configured to determine a viscosity of the exudate based upon information from the sensor.

* * * * *